US005989805A

United States Patent [19]

Reilly et al.

[11] Patent Number: 5,989,805

[45] **Date of Patent: *Nov. 23, 1999**

[54] IMMORTAL AVIAN CELL LINE TO GROW AVIAN AND ANIMAL VIRUSES TO PRODUCE VACCINES

[75] Inventors: John David Reilly, Lansing; Daniel C. Taylor, East Lansing; Roger Maes, Okemos; Paul M. Coussens, Lansing, all of Mich.

[73] Assignee: Board of Trustees operating Michigan State University, East Lansing, Mich.

[ * ] Notice: This patent is subject to a terminal disclaimer.

[21] Appl. No.: 08/967,716

[22] Filed: Nov. 10, 1997

Related U.S. Application Data

[63] Continuation-in-part of application No. 08/670,272, Jun. 21, 1996, Pat. No. 5,833,980, which is a continuation-in-part of application No. 08/549,045, Oct. 27, 1995, Pat. No. 5,827, 738.

[51] Int. Cl.[6] .......................... C12Q 1/70; A61K 39/255; C12N 5/06

[52] U.S. Cl. ............................ 435/5; 424/229.1; 435/349

[58] Field of Search ................................ 435/5, 7.1, 349; 424/204.1, 209.1, 211.1, 214.1, 215.1, 216.1, 222.1, 229.1, 232.1, 233.1

[56] References Cited

U.S. PATENT DOCUMENTS

| | | | |
|---|---|---|---|
| Re. 33,164 | 2/1990 | Brown et al. | 424/209.1 |
| 3,629,396 | 12/1971 | Yates et al. | 424/89 |
| 4,302,444 | 11/1981 | Baxendale | 424/89 |
| 4,357,320 | 11/1982 | Apontoweil et al. | 424/89 |
| 4,530,831 | 7/1985 | Lutticken et al. | 424/89 |
| 4,673,572 | 6/1987 | De Boer | 424/89 |
| 4,795,635 | 1/1989 | Peleg et al. | 424/89 |
| 5,192,539 | 3/1993 | Van Der Marel et al. | 424/201.1 |
| 5,443,982 | 8/1995 | Welniak et al. | 435/235.1 |

OTHER PUBLICATIONS

Woods et al. (1976) Antigenicity of inactivated swine influenza virus concentrated by centrifugation. Res. Comm. Chem. Pathol. Pharmacol. 13:129–132, Feb. 1976.
Brugh et al. (1979) Immunization of chickens and turkeys against avian influenza with monovalent and polyvalent oil emulsion vaccines. Am. J. Vet. Res. 40:165–169, Feb. 1979.
Alexander, D.J., Newcastle disease and other paramyxovirus infections. In:Diseases of Poultry.Ninth Edition.B.W. Calnek, et al., eds. Iowa State University Press, Ames. IA, USA 496–519 (1991).
Olson, N.O., Reovirus Infections. In:Diseases of Poultry. Ninth Edition.B.W. Calnek, et al eds. Iowa State University Press, Ames, IA, USA 639–647 (1991).
Sahu, S.P. and N. O. Olson, American Journal of Veterinary Research, vol. 36 pp. 847–850 (1975).
Barta, V., et al.,Avian Diseases, vol. 28, pp. 216–223 (1984).
Van der Heide, L., et al. Avian Diseases, vol. 27, pp. 698–706 (1983).
Rau, W.E., et al., Avian Diseases, vol. 24, pp. 648–657 (1980).
Tripathy, D.N., Pox. In: Diseases of Poultry. Ninth Edition. B.W. Calnek, et al., eds. Iowa State university Press, Ames, IA, USA pp. 583–596 (1991).
Moscovici, et al, Cell, vol. 11, pp. 95–103 (1977).
Hitchner, S.B., Avian Diseases, vol. 25, pp. 874–881 (1981).
Winterfield, R.W., Poultry Science, vol. 64, pp. 65–70 (1985).
Easterday, B.C. and V.S. Hinshaw, Influenza. In: Diseases of Poultry. Ninth Edition.B.W. Calnek, et al., eds. Iowa State University Press, Ames, IA, USA pp. 532–551 (1991).
Stone, H.D.,Avian Disease, vol. 31, pp. 483–490 (1987).
Easterday, B.C. and V. Hinshaw, Swine Influenza. In: Diseases of Swine. 7th Edition.A.D. Leman, et al., eds. Iowa State University Press, Ames, IA, USA pp. 349–357 (1992).
Hirai, K., et al. Avian Diseases, vol. 23, pp. 148–163 (1978).
Hitchner, S.B., and B.W. Calnek. American Journal of Veterinary Research, vol. 41, pp. 1280–1281 (1980).
Vindevogel, H. and J. P. Duchatel (Miscellaneous herpesvirus infection. In:Diseases of Poultry. Ninth Edition.B.W. Calnek, et al., eds. Iowa State University Press, Ames, IA, USA pp. 665–667 (1991).
Aini, I, et al., Journal of Wildlife Diseases, vol. 29, pp. 196–202 (1993).
Luckert, P.D. and Y.M. Saif; Infectious bursal disease. In: Diseases of Poultry. Ninth Edition.B.W. Calnek, et al., eds. Iowa State University Press, Ames, IA, USA pp. 648–663 (1991).
Cowen, B.S. and M.O. Braune. Avian Diseases, vol. 32, pp. 282–297 (1988).
Jackwood,et al., Avian Diseases, vol. 31, pp. 370–375 (1987).
Skeeles, J.K. and P.D.Lukert. Avian Diseases, vol. 24, pp. 43–47 (1980).
Stoll, R., et al. Journal of General Virology, vol. 75, pp. 2261–2269 (1994).
King, D.J. and D. Cavanaugh; Infectious bronchitis. In: Diseases of Poultry. Ninth Edition.B.W. Calnek, et al., eds. Iowa State University Press, Ames, IA, USA pp. 471–484 (1991).
Noteborn, M. and G. Koch. Avian Pathology. vol. 24, pp. 11–31 (1995).
Calnek, B.W., et al; Avian Encephalomyelitis. In: Diseases of Poultry. Ninth Edition.B.W. Calnek, et al., eds. Iowa State University Press,Ames,IA,USA pp. 520–531 (1991).

(List continued on next page.)

*Primary Examiner*—Nancy Degen
*Assistant Examiner*—Robert Schwartzman
*Attorney, Agent, or Firm*—Ian C. McLeod

[57] ABSTRACT

Method of propagating viruses that replicate in embryonated eggs or in primary cultures of chicken embryo cells on an immortal, virus-free, contact-inhibited, and non-oncogenic chicken embryo cell line. The method supports replication of avian viruses of the Birnaviridae, Coronaviridae, Herpesviridae, Orthomyxoviridae, Paramyxoviridae, Picornaviridae, Polyomaviridae, Poxviridae, and Reoviridae families. The immortal cell line of the present invention supports replication of swine influenza virus, for instance. The cell line is useful for virus isolation diagnostic assays and for propagating virus suitable for live or killed vaccines.

26 Claims, 8 Drawing Sheets

OTHER PUBLICATIONS

McFerran,J.B., Adenovirus (group I)infections of chickens. In: Diseases of Poultry. Ninth Edition.B.W.Calnek, et al., eds. Iowa State University Press, AMes, IA, USA pp. 552–563 (1991).

Domermuth, C.H. and W.B. Gross (Hemorrhagic enteritis and related infections. In: Diseases of Poultry. Ninth Edition.B.W.Calnek, et al., eds. Iowa State University Press, Ames, IA, USA pp. 567–672 (1991).

McFarren, J.B.(Egg drop Syndrome. In: Diseases of Poultry. Ninth Edition.B.W. Calnek, et al., eds. Iowa State University Press, Ames, IA, USA pp. 573–582 (1991).

Hayami,M., et al., International Journal of Cancer, vol. 20, pp. 729–737 (1977).

Bauer, H., et al., Medical Microbiology and Immunology. vol. 164, pp. 197–205 (1977).

Ogura, H., et al, Gann, vol. 75, pp. 410–414 (1984).

Ogura, H., and T. Fujiwara,Acta Med Okayama, vol. 41, pp. 141–143 (1987).

Kawaguchi, T.,et al., Cancer Research, vol. 47, pp. 4460–4464 (1987).

Nazerian, Avian Pathology, vol. 16, pp. 527–544 (1987).

Nick, et al.,Journal of Virology, vol. 18, pp. 227–234 (1976).

Cursiefen et al.,Archives of Virology, vol. 59, pp. 39–46 (1979).

Chettle et al.,British Veterinary Journal, vol. 141, pp. 141–145 (1985).

IMMORTAL AVIAN CELL LINE TO GROW AVIAN AND ANIMAL VIRUSES TO PRODUCE VACCINES

CROSS-REFERENCE TO RELATED APPLICATIONS

This application is a continuation-in-part of U.S. application Ser. No. 08/670,272, filed Jun. 21, 1996, U.S. Pat. No. 5,833,980, which in turn is a continuation-in-part of U.S. application Ser. No. 08/549,045, filed Oct. 27, 1995, U.S. Pat. No. 5,827,738.

FIELD OF THE INVENTION

The objects of the present invention include providing: methods for cultivating a plurality of avian or animal viruses in an immortal chick embryo cell line; immortal chick embryo cell lines infected with any one of the plurality of avian or animal viruses; methods for producing vaccines for providing immunity against any one of the plurality of avian or animal viruses, and methods for identifying any one of the plurality of avian or animal viruses.

The plurality of avian and animal viruses are viruses selected from the group comprising: avian influenza virus, swine influenza virus, equine influenza virus, Newcastle disease virus, psittacine herpesvirus, falcon herpesvirus, pigeon herpesvirus, canary pox virus, fowl pox virus, quail pox virus, pigeon pox virus, avian polyomavirus, avian reovirus and CEF-or cell culture-adapted strains of infectious bursal disease virus, avian encephalomyelitis virus, infectious bronchitis virus, and avian adenovirus.

BACKGROUND OF THE INVENTION

The following viruses are examples of viruses that are propagated in embryonated eggs or in primary cultures of chicken embryo fibroblasts prepared from embryonated eggs: avian influenza virus, avian reovirus, fowlpox virus, psittacine herpesvirus (Pachecco's herpesvirus), swine influenza virus, equine influenza virus, Newcastle disease virus, falcon herpesvirus, pigeon herpesvirus, infectious bursal disease virus, infectious bronchitis virus, Marek's disease virus, turkey herpesvirus, chicken anemia virus, avian encephalomyelitis virus, pigeon pox virus, canary pox virus, quail pox virus, avian polyomavirus types I and II, and avian adenovirus types I, II, and III. Detection of any one of these viruses as the etiological agent for a diseased animals can be determined by serological based assays or unequivocally by virus isolation (VI) diagnostic assays. For many of these viruses, live or killed vaccines are available to protect the animal from infection by the aforementioned viruses.

Vaccines comprising any of the aforementioned viruses are prepared by infecting embryonated chicken eggs or primary cultures of chicken embryo fibroblast (CEF) cells or a mammalian cell line in the case of infectious bursal disease virus (P. Van Der Marel and P. G. Mooren, U.S. Pat. No. 5,192,539). However, primary CEF cell cultures or embryonated eggs suffer from the disadvantage that theses substrates are prone to contamination with not easily detected viruses of which the probability cannot always be established prior to the actual use. Therefore, purity of vaccines prepared using these substrates cannot be established until after the preparation of the vaccine. Primary cell cultures and embryonated eggs depend on a reliable supply of embryonated eggs which can be obtained from commercial suppliers that maintain specified pathogenfree (SPF) flocks of chickens, chickens completely free of viral and bacterial contamination. However, it is difficult to continually maintain SPF flocks completely free of infection which is evidenced by the periodic outbreaks of disease in SPF flocks. The cost of SPF embryonated eggs, the cost of preparing CEF cells from embryonated eggs, and the cost of maintaining SPF flocks of chickens is expensive and reflects approximately 40% of the cost of vaccines prepared from embryonated eggs or CEF cells. Additional costs are incurred by vaccine manufacturers producing vaccines comprising any of the aforementioned viruses. Vaccine manufacturers must hold from sale every vaccine lot that is produced until the SPF supplier verifies that the chickens and the eggs produced by the chickens used to manufacture the vaccine lot were completely free of any disease. If the flock is found to have been infected, not only is the entire vaccine lot in question destroyed, the vaccine lots prior and subsequent to the vaccine lot are destroyed as well. This uncertainty adds a significant cost to the preparation of these vaccines.

Virus isolation diagnostic laboratories use embryonated SPF eggs to identify any of the aforementioned viruses. Since all of these viruses replicate well in embryonated eggs and the diagnostic laboratories do not need to prepare large quantities of virus, the expense of preparing CEF cells to detect or isolate the aforementioned viruses is unwarranted. However, VI diagnostic laboratories experience the same contamination problems experienced by vaccine manufacturers that rely on embryonated eggs. While several of the aforementioned viruses will replicate on mammalian cell lines, virus growth is poor and is limited to particular strains of virus adapted to grow on the cell line. Therefore, these cell lines have little utility in VI laboratories.

Vaccine manufacturers and VI diagnostic laboratories have long desired to replace their reliance on embryonated eggs with an immortal cell line. An immortal avian cell line would significantly reduced the cost of vaccine manufacture and the cost of VI diagnostic assays by eliminating the reliance on SPF embryonated eggs and the risk of contamination by adventitious agents either in the egg or during the preparation of primary cultures of CEF cells. An immortal avian cell line would enable for the first time the virus growing substrate to qualified by governmental regulatory agencies thereby avoiding many of the requirements currently in place. Both vaccine manufacturers and diagnostic laboratories would require the cell line to be avian in origin to ensure, in the case of VI diagnostic laboratories that the widest range of viruses could be detected, and in the case of vaccine manufacturers that the vaccine virus would be less likely to loss its potency. It is well known that viruses propagated in heterologous cells or cell lines can become incapable of replicating in the natural host. Furthermore, the viral antigens necessary for eliciting an effective immune response are altered during replication in the heterologous cell rendering vaccines made with the resulting virus ineffective. Vaccine manufacturers would also require the cell line to be completely virus free and non-oncogenic or non-tumorigenic in order to minimize the risk of inadvertently introducing viruses or transforming factors to the vaccine or vaccine virus and thereby into the vaccine recipient.

Many immortal cell lines derived from tissues of animal and human origin have been made. These cell lines have been established by chemical mutagenesis, viral transformation, directly from tumors, or have arisen unpredictably and spontaneously from primary cell cultures. However, cell lines that are virally transformed have no utility for vaccine production or VI diagnostic assays, cell lines established from tumors have little probability of being used for vaccines but may be used in some cases for VI diagnostic assays. Cell lines established by chemical mutagenesis or that occur "spontaneously" from primary cell cultures may be suitable for vaccines and VI diagnostic assays. However, some of these cell lines have subsequently been found to harbor retroviruses or have been found to be tumorigenic. The immortal cell line of the present invention contains neither any known virus nor is the cell line tumorigenic.

Current methods for propagating viruses that rely on embryonated eggs or primary cultures of CEF cells are recited next.

Newcastle Disease Virus

Newcastle disease virus (NDV), a member of the Paramyxoviridae family and one of nine recognized serogroups of avian paramyxoviruses, is one of the most important pathogens for poultry. However, other paramyxovirus serotypes can cause serious disease as well. NDV and other avian paramyxoviruses are reviewed by D. J. Alexander (Newcastle disease and other paramyxovirus infections. In: Diseases of Poultry. Ninth Edition. B. W. Calnek, et al., eds. Iowa State University Press, Ames, Iowa, USA (1991) pp. 496–519). There are three NDV pathotypes based on virulence lentogenic, mesogenic, and velogenic. The lentogenic pathotype is the least virulent and velogenic the most virulent.

NDV can replicate in many primary cell types and many non-avian cell lines, however plaque formation and therefore replication is generally poor in most of these cell systems and appears to be related to virulence of the particular NDV strain. For example, in primary cultures of chick embryo cells plaque formation is restricted to velogenic and mesogenic viruses unless $Mg^{++}$ ions and DEAE or trypsin are added to the culture as an agar overlay. These limitations make cell culture systems inconvenient for virus isolation assays for identification of NDV and impractical for making NDV vaccines. Therefore, virus isolation assays to identify NDV (or other avian paramyxoviruses) are performed using embryonated eggs obtained from specific pathogen-free (SPF) flocks of chickens.

Propagation of avian paramyxoviruses is as follows. Embryonated eggs are held for 9 to 10 days at before inoculation of the allantoic cavity with chicken samples (6 to 7 day old eggs are used to isolate other avian paramyxoviruses). The eggs are incubated for 4 to 7 days and then the allantoic fluid or amniotic fluid is harvested. Usually, the harvested fluid is passaged at least one more time in eggs before analysis. Virus is detected by testing the fluid by an hemagglutination assay (HA). Since HA activity may be caused by any of the paramyxovirus serotypes or by avian influenza virus, an hemagglutination-inhibition (HI) test with polyclonal or monoclonal antibodies against NDV (or other avian paramyxovirus) is then performed to specifically identify the virus as NDV (or other avian paramyxovirus).

Embryonated eggs are used for the preparation of both live and inactivated NDV vaccines. Primary avian cell cultures or non-avian cell lines are impractical for growing NDV at the scale necessary for producing vaccines since vaccines containing lentogenic strains need to be overlaid with agar containing $Mg^{++}$ ions and DEAE or trypsin to get development of CPE and good virus production. Live NDV vaccines are made from viruses from the lentogenic group (V4, Hitchner B1, F Asplin, or La Sota strains) or the mesogenic group (Roakin, Komarov, Mukteswar, or H strains). Lentogenic-based vaccines because of their low virulence can be used for initial vaccination of chickens and mesogenic-based vaccines because of their greater virulence are only suitable for secondary vaccination of chickens. Live vaccines consist of freeze-dried allantoic fluid from infected embryonated eggs and are usually administered in the drinking water or as an aerosol or spray.

Inactivated virus vaccines are usually produced from infected allantoic fluid treated with betapropriolactone or formalin to kill the virus and then mixed with a carrier adjuvant. NDV strains used for production of inactivated vaccines include Ulster 2C, B1, La Sota, Roakin, and several virulent viruses. Vaccination of killed vaccines are administered by injection, either subcutaneously or intramuscularly.

Avian Reovirus

Avian reovirus, a member of the Reoviridae family, infects chickens and has been reviewed by J. K. Rosenberger and N. O. Olson (Reovirus Infections. In: Diseases of Poultry. Ninth Edition. B. W. Calnek, et al., eds. Iowa State University Press, Ames, Iowa, USA (1991) pp. 639–647). Avian reovirus can grow in a variety of primary avian cells from the lung, kidney, liver, macrophage, or testicle of 2 to 6 week old chickens however primary embryo liver cells are preferred. Avian reovirus can be adapted to replicate in chicken embryo fibroblast (CEF) cells. Avian reovirus has been grown on established non-avian cell lines, albeit poorly (S. P. Sahu and N. O. Olson (1975). American Journal of Veterinary Research, Vol. 36, pp. 847–850; V. Barta, et al. (1984). Avian Diseases, Vol. 28, pp. 216–223).

Virus isolation assays to identify avian reovirus is performed in eggs. Nine to 11 day old eggs are inoculated by the chorianonic membrane (CAM) route. The eggs are incubated for 7 days after which the CAMs are harvested. The CAMs are homogenized and used as antigen in agar-gel precipitin tests or enzyme-linked immunosorbent assays (ELISA) using antibodies against avian reovirus.

Avian reovirus vaccines comprise viable attenuated virus prepared from inoculated eggs and is usually administered subcutaneously (L. Van der Heide, et al.(1983). Avian Diseases, vol. 27, pp. 698–706; W. E. Rau, et al. (1980). Avian Diseases, vol. 24, pp. 648–657).

Avian Pox Viruses

Avian pox viruses are member of the Poxviridae genus is reviewed by D. N. Tripathy (Pox. In: Diseases of Poultry. Ninth Edition. B. W. Calnek, et al., eds. Iowa State University Press, Ames, Iowa, USA (1991) pp. 583–596). Fowl pox virus, canary pox virus, quail pox virus, and pigeon pox virus are examples of avian pox viruses. Avian poxviruses can be grown in primary avian cell cultures of which CEF cells are an example. Some avian poxviruses after adaptation will grow on an immortal Japanese quail cell line QT-35 (Moscovici, et al. (1977). Cell, vol. 11, pp. 95–103) however since only some avian pox viruses will grow on QT-35 after adaptation, the cell line is not practical for virus isolation assays. In addition, since the QT-35 cell line causes tumors in chickens, the cell line has not been used to make poultry vaccines.

Identification and isolation of avian pox viruses comprise inoculation of the CAM of 9 to 12 day old eggs. Five to 7 days post-inoculation the CAMs are examined for pox lesions. Cell culture is not employed for identification and isolation of avian pox viruses since adaptation of the virus to cell culture is often necessary.

Fowl pox vaccines are either prepared from infected CAMs or on primary cultures of CEF cells. Live fowl pox vaccines of CAM origin are not attenuated and can be administered to the wing-web of 4 week-old chicks and pullets about one to two months before egg production. Attenuated fowlpox vaccines of primary CEF cells origin can be administered to one-day old chicks. Recombinant fowl pox vaccines are usually prepared on primary cultures of CEF cells.

Pigeon pox vaccines prepared from infected CAMs comprise non-attenuated live pigeon pox virus. Pigeon pox virus vaccines can be used on 4 week-old chickens and pullets about one month before egg production, turkeys of any age, and pigeons.

Canary pox vaccines comprise live attenuated canary pox prepared from infected CAMs and has been used experimentally in the United States (S. B. Hitchner (1981). Avian Diseases, vol. 25, pp. 874–881) and are commercially available. Recently, there has been considerable interest in developing recombinant canary pox vaccines for use in humans.

Quail pox vaccines are prepared from infected CAMs and are commercially available for use in quails (R. W. Winterfield (1985). Poultry Science 64:65–70 (1985)).

Avian Influenza

Avian influenza virus is a member of the Orthomyxoviridae family and is reviewed by B. C. Easterday and V. S. Hinshaw (Influenza. In: Diseases of Poultry. Ninth Edition. B. W. Calnek, et al., eds. Iowa State University Press, Ames, Iowa, USA (1991) pp. 532–551). All strains of avian influenza will replicate to high titers in nine to ten day-old embryonated chicken eggs. Avian influenza virus can replicate in primary cultures of CEF cells or in continuous mammalian cell lines however an agar overlay containing trypsin needs to be added to the cell culture monolayer to get production of infectious virus.

Isolation of avian influenza virus for identification and large-scale production of influenza virus is performed by inoculating ten to eleven day-old embryonated eggs. Approximately three days post-inoculation the allantoic fluid is collected and tested for hemagglutination activity (HA). HA positive samples are tested in a hemagglutinating inhibition assay (HI) with antibody against NDV to rule out NDV contamination. HI negative samples are tested for influenza type with type-specific antibodies by enzyme-linked immunoadsorbant assay (ELISA), followed by ELISA to determine the antigenic subtype of the influenza virus.

Avian influenza vaccines are inactivated vaccines made from infected allantoic fluid (H. D. Stone (1987). Avian Disease, vol. 31, pp. 483–490).

Swine Influenza

Swine influenza is an Orthomyxovirus and has been reviewed by B. C. Easterday and V. Hinshaw (Swine Influenza. In: Diseases of Swine. 7$^{th}$ Edition. A. D. Leman, et al., eds. Iowa State University Press, Ames, Iowa, USA (1992) pp. 349–357). Swine influenza virus will replicate in a wide variety of primary cells and cell lines in the presence of an agar overlay containing trypsin, however the embryonated egg is the culture system most commonly used to propagate swine influenza virus. Isolation of swine influenza virus for identification and large-scale production of influenza virus is performed by inoculating ten day-old embryonated eggs. Approximately three to four days post-inoculation the allantoic fluid is collected and tested for hemagglutination activity (HA). HA positive samples are tested in a hemagglutinating inhibition assay (HI) to determine the hemagglutinin subtype and a neuraminidase inhibition assay (NI) to determine the neuraminidase subtype.

Inactivated swine influenza vaccines are prepared from embryonated ten day-old eggs and a vaccine is commercially available.

Psittacine Herpesvirus

Psittacine herpesvirus, a member of the Herpesviridae family, is a highly fatal disease of parrots and other psittacine birds. Psittacine herpesvirus can replicate in embryonated eggs, primary cultures of CEF and chick kidney cells (K. Hirai, et al. (1978). Avian Diseases, vol. 23, pp. 148–163). A psittacine inactivated vaccine prepared on primary cultures of chick kidney cells has been described (S. B. Hitchner and B. W. Calnek (1980). American Journal of Veterinary Research, vol. 41, pp. 1280–1282) and an inactivated vaccine is commercially available.

Pigeon and Falcon Herpesvirus

Pigeon herpesvirus and falcon herpesvirus, members of the Herpesviridae family, are serologically related and have been reviewed by H. Vindevogel and J. P. Duchatel (Miscellaneous herpesvirus infection. In: Diseases of Poultry. Ninth Edition. B. W. Calnek, et al., eds. Iowa State University Press, Ames, Iowa, USA (1991) pp. 665–667). Pigeon and falcon herpesviruses are serologically related, DNA restriction enzyme analysis demonstrated their genomes have similar DNA cleavage pattens, and can be propagated in primary cultures of CEF (I. Aini, et al. (1993). Journal of Wildlife Diseases, vol. 29, pp. 196–202). A live pigeon herpesvirus vaccine of chicken embryo origin is available for pigeons, chickens and turkeys.

Infectious Bursal Disease Virus

Infectious bursal disease virus, a member of the Birnaviridae family, infects both chickens and turkeys and has been reviewed by P. D. Luckert and Y. M. Saif (Infectious bursal disease. In: Diseases of Poultry. Ninth Edition. B. W. Calnek, et al., eds. Iowa State University Press, Ames, Iowa, USA (1991) pp. 648–663). Many strains of infectious bursal disease virus have been adapted to primary cell cultures of chicken origin, Japanese quail QT35 cell line (B. S. Cowen and M. O. Braune (1988). Avian Diseases, vol. 32, pp. 282–297) and to several mammalian cell lines (Jackwood, et al. (1987). Avian Diseases, vol. 31, pp. 370–375). Infectious bursal disease virus vaccines are prepared from attenuated viruses produced on CEF cells (J. K. Skeeles and P. D. Lukert (1980). Avian Diseases, vol 24, pp. 43–47) or Vero cells (P. Van Der Marel and P. G. Mooren, U.S. Pat. No. 5,192,539).

Avian Polyomavirus

Avian polyomavirus (budgerigar fledgling disease), a member of the Polyomaviridae family, comprises three types. Type I causes an acute lethal disease in budgerigars, type II infects chickens but has not been identified as causing disease in chickens, and type III causes acute lethal disease in macaws (R. Stoll, et al. (1994). Journal of General Virology, vol. 75, pp. 2261–2269).

Types I and II can replicate in primary cultures of CEF cells whereas type III can replicate only one round. An inactivated vaccine is available.

Infectious Bronchitis Virus

Infectious bronchitis virus is a member of the Coronaviridae family and is reviewed by D. J. King and D. Cavanaugh (Infectious bronchitis. In: Diseases of Poultry. Ninth Edition. B. W. Calnek, et al., eds. Iowa State University Press, Ames, Iowa, USA (1991) pp. 471–484). Infectious bronchitis virus can be propagated in embryonated eggs, primary cultures of chick embryo kidney cells, chicken embryo fibroblasts, chicken kidney cells and embryo tracheal organ cultures. Various strains have been adapted to the Vero cell line.

Diagnosis of infectious bursal disease by VI is performed in embryonated eggs or embryo tracheal organ cultures. Both inactivated and attenuated live virus vaccines are commercially available.

Chicken Anemia Virus

Chicken anemia virus causes transient severe anemia in young chickens and is recognized as an important poultry pathogen (reviewed in M. Noteborn and G. Koch (1995). Avian Pathology, vol 24, pp. 11–31). Chicken anemia virus has not been classified by taxonomists. Chicken anemia virus can be propagated in chicken embryos and in chicken cell lines that have been immortalized by Marek's disease virus or avian leukosis virus.

Avian Encephalomyelitis Virus

Avian encephalomyelitis virus has not been formally classified by taxonomists but may be a member of the Picornaviridae family. B. W. Calnek, et al. has reviewed avian encephalomyelitis virus (Avian Encephalomyelitis. In: Diseases of Poultry. Ninth Edition. B. W. Calnek, et al., eds. Iowa State University Press, Ames, Iowa, USA (1991) pp. 520–531). The virus can be propagated in the yolk sac of embryonated eggs or primary chick neuroglial cell cultures.

Detection of avian encephalomyelitis virus is performed by inoculating 5 to 7 day old eggs, allow the eggs to hatch, and observe the chicks for the first 10 days. If clinical signs appear, the brain, proventriculus, and pancreas are removed and examined by histology, and the duodenum is examined for specific viral antigens by fluorescent antibody assays.

Both inactivated and attenuated live virus vaccines prepared from embryonated eggs are commercially available.

Avian Adenovirus

Avian adenovirus encompasses a wide range of viruses that can be catalogued into three groups, I, II, and egg drop syndrome virus. Group I avian adenoviruses are reviewed by J. B. McFerran (Adenovirus (group I) infections of chickens. In: Diseases of Poultry. Ninth Edition. B. W. Calnek, et al., eds. Iowa State University Press, Ames, Iowa, USA (1991) pp. 552–563, group II adenoviruses are reviewed by C. H. Domermuth and W. B. Gross (Hemorrhagic enteritis and related infections. In: Diseases of Poultry. Ninth Edition. B. W. Calnek, et al., eds. Iowa State University Press, Ames, Iowa, USA (1991) pp. 567–572), and egg drop syndrome virus is reviewed by J. B. McFarren (Egg drop Syndrome. In: Diseases of Poultry. Ninth Edition. B. W. Calnek, et al., eds. Iowa State University Press, Ames, Iowa, USA (1991) pp. 573–582.

Group I viruses can be propagated in primary chicken embryo kidney or liver cell cultures and not at all in CEF cells or tracheal organ cultures. Type I adenoviruses are not perceived as a health threat therefore, type I vaccines are not available.

Group II virus, hemorrhagic enteritis virus of turkeys can be propagated in a turkey lymphoblastoid tumor cell line and in turkey leukocytes. A related group II virus afflicting chickens is marble spleen disease virus (avian adenovirus splenomegaly virus). A vaccine is available for hemorrhagic enteritis virus of turkeys.

Egg drop syndrome virus can be propagated in embryonated duck or goose eggs and primary cultures of duck embryo kidney, liver, or fibroblasts, chicken embryo liver and kidney cells, poorly in CEF cells and not at all in embryonated chicken eggs. Embryonated duck or goose eggs provide the most sensitive method of detection. An inactivated vaccine is commercially available.

SUMMARY OF THE INVENTION

The invention relates to the use of an immortal, contact-inhibited and non-oncogenic chick embryo cell line that is virus free as a method to propagate avian and animal viruses that previously could only be effectively propagated on primary cultures of chicken embryo fibroblast (CEF) cells or in embryonated chicken eggs.

The present invention is useful for virus isolation (VI) diagnostic assays that depend on embryonated eggs or primary cultures of CEF cells.

The present invention is useful for producing avian or animal viruses for serological based assays, hemagglutination based assays, or PCR.

The invention is useful for preparing live avian and animal vaccines that depend on a embryonated eggs or primary cultures of primary CEF cells for producing the virus used for the vaccine.

The invention is useful for preparing inactivated avian and animal vaccines that depend on embryonated eggs or primary cultures of primary CEF cells for producing the virus used for the vaccine.

The invention is the first immortal chicken embryo cell line that is virus-free, contact-inhibited, and non-oncogenic which supports replication of a plurality of viruses that previously were restricted to propagation in embryonated eggs or primary cultures of CEF cells.

The foregoing merely summarizes certain aspects of the present invention and is not intended, nor should be construed, as limiting the invention in any manner. All patents and cited herein establish the state of art and are hereby incorporated by reference in their entirety.

DESCRIPTION OF PREFERRED EMBODIMENTS

Figure 1A:
FIG. 1A is a photomicrograph of an uninfected showing CHCC-OU2 cells reacted with chicken anti-avian influenza virus antiserum and stained with rabbit anti-chicken IgG horseradish peroxidase conjugated antibodies.

The present invention relates to a vaccine, comprising: a virus that can replicate in chicken embryo fibroblasts derived from an immortal chicken embryo cell line infected with the virus, wherein said vaccine is free of the chicken embryo cell line and induces a protective immune response when administered to a host animal.

Further, the present invention relates to an avian vaccine, comprising: an avian virus derived from an immortal chicken embryo cell line infected with the avian virus, wherein the vaccine is free of the chicken embryo cell line and induces a protective immune response when administered to an avian.

The present invention provides a method for propagating any one of a plurality of avian or animal viruses comprising: (i) providing an immortal chicken embryo cell line, wherein the cell line is derived from chicken embryo cells treated with a chemical mutagen to render the cells immortal, (ii) infecting the immortal cell line with any one of a plurality of avian or animal viruses, (iii) culturing the said infected cell line, and (iv) recovering said viruses produced thereby.

The present invention provides a method for propagating any one of a plurality of avian or animal viruses comprising: (i) providing the immortal chicken embryo cell line CHCC-OU2, (ii) infecting the immortal cell line with any one of a plurality of avian or animal viruses, (iii) culturing the said infected cell line, and (iv) recovering said viruses produced thereby.

The invention provides a method for producing modified or attenuated avian or animal viruses for a live attenuated virus vaccine from any one of a plurality of avian or animal viruses comprising: (i) providing an immortal chicken embryo cell line wherein the cell line is derived from chicken embryo cells treated with a chemical mutagen to render the cells immortal, (ii) infecting the cell line with one of a plurality of avian or animal viruses, (iii) propagating the virus for a multiplicity of cell culture passages to render the virus attenuated, and (iv) harvesting the attenuated virus.

The invention provides a method for producing modified or attenuated avian or animal viruses for a live attenuated virus vaccine from any one of a plurality of avian or animal viruses comprising: (i) providing the immortal chicken embryo cell line CHCC-OU2, (ii) infecting the cell line with one of a plurality of avian or animal viruses, (iii) propagating the virus for a multiplicity of cell culture passages to render the virus attenuated, and (iv) harvesting the attenuated virus.

The present invention relates to the use of an immortal, contact-inhibited and non-oncogenic chick embryo cell line that is virus free as a method to propagate avian and animal viruses that previously could only be effectively propagated on primary cultures of chicken embryo fibroblast (CEF) cells or in embryonated chicken eggs. The invention is useful for virus isolation (VI) diagnostic assays that depend on embryonated eggs. The invention is useful for preparing avian and non-avian viruses vaccines that depend on a embryonated eggs for producing the vaccines or for preparing primary cultures of primary CEF cells that are then used for producing the vaccines. The invention is the first immortal chicken embryo cell line made by chemical mutagenesis that is virus-free, contact-inhibited, and non-oncogenic that supports replication of a plurality of viruses that previously were restricted to propagation in embryonated eggs or primary cultures of CEF cells.

Many avian cell lines that have been described: Japanese quail cell lines made from tumors isolated from the muscles of young birds that had been treated with 20-methylcholanthrene (C. Moscovici, et al. (1977). Cell, vol. 11, pp. 95–103) and retroviruses (M. Hayami, et al. (1977). International Journal of Cancer, vol. 20, pp. 729–737); H. Bauer, et al. (1977). Medical Microbiology and Immunology, vol. 164, pp. 197–205), chick embryo cell lines made by chemical mutagenesis of 11 day old chick embryos (H. Ogura, et al. (1984). GANN, vol 75, pp. 410–414; H. Ogura and T. Fujiwara (1987). Acta Med Okayama, vol. 41, pp. 141–143), spontaneously arising chick embryo cell lines (H. Ogura, et al. ibid.), chicken tumor cell lines made by chemical mutagenesis (T. Kawaguchi, et al. (1987). Cancer Research, vol. 47, pp. 4460–4464) and many avian cell lines that have been made from virally transformed cells (reviewed in Nazerian (1987). Avian Pathology, vol. 16, pp. 527–544).

Cell lines made by viral transformation (Nazerian, ibid) cannot be used for virus isolation and identification assays nor for vaccines because of the presence of the transforming virus. Furthermore, none of these cell lines have been reported to support replication of economically important viruses.

The QT-35 Japanese quail tumor cell line (Moscovici, et al. ibid) can propagate avian viruses of the Birnaviridae, Coronaviridae, Herpesviridae, Paramyxoviridae, Poxviridae, Reoviridae, and Retroviridae families (B. S. Cowen and M. O. Braune (1988). Avian Diseases, vol. 32, pp. 282–297), however QT35 cells are oncogenic when injected into birds and have not been adopted by vaccine manufacturers for vaccine production or by VI diagnostic laboratories. The CHCC-OU1 cell line derived by chemical mutagenesis and the SPCC-OU1 cell line that arose by chemical mutagenesis (H. Ogura et al. Ibid) produce avian endogenous leukosis virus and as such cannot be used for isolation and identification assays nor for vaccine production. The chicken tumor cell line, LMH (T. Kawaguchi et al. ibid.) induces tumors in chickens, however the cell line has been reported to support the replication of infectious laryngotracheitis virus for use for vaccines (E. Welniak and G. R. Petersen, U.S. Pat. No. 5,443,982), but not the replication of the aforementioned mentioned viruses.

The chick embryo cell line CHCC-OU2 derived by treatment of 11 day old chick embryo cells with a chemical mutagen (H. Ogura and T. Fujiwara, ibid) is fibroblastic, contact-inhibited, non-tumorigenic in chickens and is virus-free. The cell line supports replication of Marek's disease virus and has utility for producing Marek's disease vaccines (Coussens and Abujoub, U.S. patent application Ser. No. 08/549,945 herein incorporated by reference and Coussens, Abujoub and Reilly, U.S. patent application Ser. No. 08/670,272 herein incorporated by reference), the cell line was disclosed by H. Ogura and T. Fujiwara (ibid.) to support replication of subgroup A avian retroviruses. H. Ogura and T. Fujiwara (ibid.) made a non-enabling disclosure that the cell line could support replication of the Italian strain of Newcastle disease virus. The cell line has not been reported to support replication of any other avian or non-avian viruses.

The cell lines used in the present invention can propagate viruses of the Paramyxoviridae family, Picornaviridae family, orthomyxoviridae family, Poxviridae family, Reoviridae family, Polyomaviridae family, Birnaviridae family, and Herpesviridae family. Exemplary of viruses that can be replicated and propagated by the method of the present invention are: avian reovirus (Reovirus), fowlpox virus, pigeon pox virus, canary pox virus and quail pox virus (Pox virus), psittacine herpesvirus, falcon herpesvirus and pigeon herpesvirus (herpesvirus), swine influenza virus, avian influenza virus and equine influenza virus (Orthomyxovirus), budgerigar fledgling disease (Polyomavirus), and Newcastle disease virus (Paramyxovirus). The method of the present invention can also be envisioned to support the replication of other avian viruses such as CEF- or cell culture-adapted strains of infectious bursal disease virus (Birnavirus), CEF- or cell culture-adapted strains of infectious bronchitis virus (Coronavirus), CEF- or cell culture-adapted avian encephalomyelitis virus, cell culture adapted strains of chicken anemia virus, and CEF- or cell culture-adapted strains of avian adenovirus types I, II, and III (Adenovirus). This list of viruses is not all inclusive and is only to serve as an example of the utility of the present invention.

The invention comprises the immortal chick embryo cell line CHCC-OU2 infected with any one of the aforementioned viruses. In one embodiment of the present invention, the CHCC-OU2 cell line is used in virus isolation (VI) assays for the identification of any of the aforementioned viruses that may be etiological agent in the diseased animal. A tissue, nasal, serum, or other sample from a diseased animal is inoculated onto tissue culture dishes containing a monolayer of CHCC-OU2 cells. The inoculated CHCC-OU2 cells are incubated and upon development of cytopathic effect (CPE) which is indicative of viral infection, the infected cells are used to prepare stocks of the inoculated virus to use for virus identification by infecting a plurality of CHCC-OU2 cell monolayers and after development of CPE, reacting the infected CHCC-OU2 monolayers with a panel of virus specific antibodies, and subsequently reacting with labeled antibodies specific for the first antibody. Alternatively, the inoculated CHCC-OU2 monolayer is tested sequentially against a panel of virus-specific antibodies and subsequently reacted with labeled antibodies specific for the first antibody.

In another embodiment of the present invention, the CHCC-OU2 cell line is infected with any one of the aforementioned viruses. The cells may be a monolayer in tissue culture dishes or a monolayer in a roller bottle, or a monolayer on microcarrier beads in a bioreactor. At the appropriate time after infection the infected CHCC-OU2 cells and culture media is harvested and is used to prepare a live or inactivated vaccine against the infecting virus. Preparation of live or inactivated vaccines containing any one of the aforementioned viruses is well-known to those skilled in the art.

The CHCC-OU2 cell line of the present invention is a non-tumorigenic, contact-inhibited, fibroblastic cell line derived from chick embryo cells that were treated with the chemical mutagen methylnitronitrosoguanidine (MNNG). Chick embryo cells from embryonated eggs were treated with 10 $\mu$g/ml MNNG for 60 minutes, washed three times, and maintained in culture medium consisting of minimal essential medium supplemented with 1% heat inactivated chicken serum, 5% calf serum, and 10% tryptose phosphate broth in an incubator at 41° C. under 5% $CO_2$ atmosphere. The cells were subcultured and showed exponential growth for 28 cell culture passages wherein cell growth deteriorated. However, after the $35^{th}$ cell culture passage the cells again showed exponential growth and have continued to show exponential growth for over 300 passages. The cell line was named CHCC-OU2 by H. Ogura and T. Fujiwara (ibid).

The CHCC-OU2 cell line was obtained by the present inventors and passaged in culture medium consisting of Liebovitz's L15—McCoy's A5 supplemented with calf serum within the range of 1% to 20% (v/v) in an incubator at 37° C. under 5% $CO_2$ atmosphere. The cell line is subcultured by releasing the cells from the substrate with a dilute solution of trypsin, inactivating the trypsin with culture media supplemented with calf serum, diluted with medium and transferred to additional tissue culture dishes. The cell line may be suspended in culture medium containing 5% to 25% (v/v) calf serum and 5% to 20% (v/v) glycerol or dimethylsufoxide (DMSO), slowly frozen at rate of approximately 1° C. per minute to −70° C. and stored frozen below −70° C. for extended periods of time.

The CHCC-OU2 cell line has been allowed to incubate at high density for extended periods of time. It is well known to those skilled in the art that cell lines maintained at high density develop altered growth characteristics. During cultivation over 2 years and multiple passages, the CHCC-OU2 cell line of the present invention, CHCC-OU2 subspecies ATCC CRL 12623, has acquired characteristics that distinguish the cell line from the CHCC-OU2 cells of Ogura and Fujiwara (ibid.). The most notable acquired characteristic is that the CHCC-OU2 cell line of the present invention, subspecies ATCC CRL 12623, grows in monolayer at 37° C. from an initial seed density of $1.9\times10^5$ cells/cm$^2$ to a cell density within the range of $6.3\times10^5$ cells/cm$^2$ to $7.6\times10^5$ cells/cm$^2$ in seven to eight days, whereas CHCC-OU2 cells grow from an initial seed density of $1.9\times10^5$ cells/cm$^2$ to cell density within the range of $3.1\times10^5$ cells/cm$^2$ to $6.3\times10^5$ cells/cm$^2$ within seven to eight days. The CHCC-OU2 cell line, subspecies ATCC CRL 12623, of the present invention was demonstrated to be non-oncogenic when injected into birds, even after four months.

The CHCC-OU2 cell line has been deposited with the American Type Culture Collection (ATCC), 10801 University Boulevard, Manassas, Va. 20110-2209 under the provisions of the Budapest Treaty as accession number ATCC CRL 12302 on Feb. 26, 1997. The CHCC-OU2 subspecies cell line was deposited at the ATCC Dec. 18, 1998 under the provisions of the Budapest Treaty. The deposit was given the accession number CRL 12623. The CHCC-OU2 cell line and CHCC-OU2 subspecies cell line will be irrevocably available from the ATCC for the life of the patent.

Preparation of vaccines using the method of the present invention is performed by infecting the immortal avian cell line of the present invention with virus. The monolayers may be formed on tissue culture dishes, roller bottles, stirred vessels (fermenters), or microcarrier systems. In addition there are a multiplicity of other systems suitable for culturing cells such as bioreactors, spinner cultures, or cubes. The media used to propagate the immortal cells may be any of the commonly available tissue culture media supplemented with calf serum or fetal calf serum within the range of 1% to 20% (v/v). If desired the media may contain antibiotics. The preferred medium comprises Liebovitz's L15-McCoy's 5A (1.75:1 v/v) media supplemented with 5% calf serum. The monolayer is inoculated with any of the aforementioned viruses. Preferably the virus is an attenuated form of the virus adapted to replicate on CEF cells or attenuated virus adapted to replicate on CHCC-OU2 cells or subspecies ATCC CRL 12623. The culture fluid is harvested after the onset of cytopathic effect. The harvested culture fluid can be frozen or frozen, preferably after the addition of a stabilizer such as carbohydrates, SPGA, proteins, or other compounds known to those skilled in the arts. Alternatively, the harvested culture fluid may be lyophilized, preferably in the presence of a stabilizer. The frozen or lyophilized virus may be diluted with culture medium to provide an appropriate dose of live virus vaccine. The vaccine is then administered to the avian or animal by any of a plurality of methods which include but are not limited to inoculation intramuscularly or subcutaneously, spraying, ocularly, nasally, orally, or in ovo.

An inactivated vaccine may be prepared as well from the harvested culture fluid. Inactivation may be achieved by treating the viruses by any of the methods commonly employed to make inactivated vaccines. These methods include but are not limited to formaldehyde treatment, betapropriolactone treatment, ethylene-imine treatment, treatment with a plurality of organic solvents, treatment with a plurality of detergents, treatment with gamma radiation or X-rays, or treatment with ultraviolet light. The methods recited herein serve as art-known examples for inactivating virus. Inactivated virus vaccines are usually administered mixed with an adjuvant such as aluminum hydroxide, and an emulsifier such as oil, or a detergent. The inactivated can be administered to the animal by any of a plurality of methods which include but are not limited to inoculation intramuscularly or subcutaneously, spraying, ocularly, nasally, orally, or in ovo.

Tables I and II display the results of psittacine herpesvirus, avian influenza virus, swine influenza virus, equine influenza virus (Miami and Prague strains), avian reovirus, Newcastle disease virus, infectious bronchitis virus, avian encephalomyelitis virus, and infectious bursal disease infections of CHCC-OU2 cells or subspecies ATCC CRL 12623. CHCC-OU2 cells were seeded to wells of tissue culture dishes in media comprising Eagle's Minimal Essential Medium with Earle's salts (EMEM) containing 0.05% lactoalbumen hydrolysate (LAH) supplemented with 10% fetal bovine serum and the dishes incubated at 37° C. in a $CO_2$ atmosphere of 5%. After two days, the cells at approximately 80% confluence were inoculated with serial dilutions of the aforementioned viruses made in above media and incubated at 37° C. After 4 days, when CPE was evident, the cells were fixed to the dishes by removing the media, washing twice with 0.01 M phosphate buffered saline (PBS), pH 7.6, and fixing with IPMA fixative (35% acetone in 0.01 M PBS, pH 7.6 containing 0.02% bovine serum albumen (BSA)) for 10 minutes at room temperature. Afterwards, the fixative was removed and the fixed cells were dried in the dark at 37° C. for 90 minutes or until the fixed cells appeared visually dry. The dried fixed cells were reacted with chicken polyclonal antiserum against the appropriate virus at a 1:100 dilution in IPMA binding buffer (0.01 M PBS, pH 7.6 containing 0.05% Tween 20 (polyoxyethylene sorbitan monolaurate) and 2.95% NaCl) or in the case of swine influenza virus anti-swine influenza virus antiserum made in gnotobiotic pigs diluted 1:100 in IMPA binding buffer for one to two hours at room temperature. Afterwards, the antiserum dilutions were removed and the samples were washed three times at room temperature and at two minutes per wash with IPMA wash buffer (0.01 M PBS, pH 7.6 containing 0.05% Tween 20). Then, the samples were reacted with a 1:1000 dilution of rabbit anti-chicken IgG horseradish peroxidase conjugated antibody or in the case of swine influenza virus Protein G-horseradish peroxidase in IPMA binding buffer for fifteen minutes at room temperature. Afterwards, the rabbit anti-chicken IgG peroxidase conjugated antibody was removed and the samples washed twice at room temperature and at two minutes per wash with IPMA wash buffer. Then, the samples were incubated in the dark for one hour at room temperature in substrate solution (0.05 M sodium acetate, pH 5.0 containing 0.012% H2O2, and 6% of a solution containing 0.33% 3-amino-9 ethylcarbazole dissolved in N, N-dimethyl formamide). Finally, the plates were drained and washed twice with water and the samples stored dried.

TABLE I

| | Number of Focal Areas per Virus Dilution | | | | | |
|---|---|---|---|---|---|---|
| Virus | Neat | 1:5 | 1:25 | 1:125 | 1:625 | Control |
| Swine Influenza | ++++ | ++++ | ++++ | ++++ | +++ | – |
| Equine influenza (Miami) | + | 5 | 2 | 2–3 | – | – |
| Equine influenza (Prague) | + | 15 | 3 | 6 | – | – |
| Psittacine herpesvirus | +++ | +++ | +++ | +++ | 1 | – |

TABLE II

| | Number of Focal Areas per Virus Dilution | | | | | |
|---|---|---|---|---|---|---|
| Virus | $10^{-1}$ | $10^{-2}$ | $10^{-3}$ | $10^{-4}$ | $10^{-5}$ | Control |
| Psittacine herpesvirus | ++++ | +++ | ++ | + | – | – |
| Fowl pox virus | ++++ | +++ | ++ | + | 1 | – |
| Avian influenza | +++ | ++ | + | 30 | 1 | |
| Avian influenza | ++++ | +++ | ++ | 20–30 | 3–4 | – |
| Newcastle disease | ++++ | +++ | ++ | 20 | 5 | – |
| Newcastle disease | ++++ | ++++ | ++ | + | 20 | – |
| Avian reovirus | ++++ | +++ | 30 | 4 | – | – |
| Avian reovirus | ++++ | +++ | + | 2 | – | – |
| Infectious bursal disease | ++? | +? | – | – | – | – |
| Infectious bronchitis | – | – | – | – | – | – |
| Avian encephalomyelitis | – | – | – | – | – | – |

The stained plaques or focal areas were counted for each well. For wells too heavily infected to count the plaques or focal areas, the degree of infection was assigned "+" marks, with the relative intensity of infection ranging from extremely infected (++++) to lightly infected (+). No infection detected was assigned "–." Psittacine herpesvirus, avian influenza virus, swine influenza virus, equine influenza virus (Miami and Prague strains), avian reovirus, and Newcastle disease virus replicated well, infectious bursal disease virus appeared to replicate but the results were not unequivocal (indicated by the "?" mark), and avian encephalomyelitis virus and infectious bronchitis virus replication was not detected. However, infectious bursal disease virus, infectious bronchitis virus, and avian encephalomyelitis virus adapted to replicate on CEF cells are expected to replicate on CHCC-OU2 cells by the method present invention for use as vaccines. Furthermore, the aforementioned viruses can be adapted to replicate on CHCC-OU2 cells or attenuated on CHCC-OU2 cells by the method of the present invention for use as vaccines.

The invention will be further illustrated in detail in the following by means of examples. The CHCC-OU2 subspecies used in all the following examples was ATCC CRL 12623.

EXAMPLE 1

Replication of Fowl Pox Virus on Immortal Chicken Cell Line of the Present Invention The purpose of this experiment was to determine whether fowl pox virus could replicate on CHCC-OU2 cell monolayers. While it is known that avian pox viruses will replicate on primary cultures of CEF cells, it was unknown whether fowl pox could replicate on CHCC-OU2 cells because CHCC-OU2 cells had been chemically mutagenized which induced unknown changes in the cells that rendered the cells immortal but with a doubling time four times slower than CEF cells that could affect susceptibility of the cells to avian pox virus infection and replication. Even though the CHCC-OU2 cells appear to have a morphology similar to CEF cells, Japanese quail QT-35 cells also appear to have a morphology similar to CEF cells but in the case of QT-35 cells avian pox virus replication is limited to some avian pox viruses and only after adaptation to the QT-35 cell line. Therefore, the following experiment was performed to determine whether avian pox viruses could replicate on CHCC-OU2 cells.

Monolayers of CHCC-OU2 cells were seeded to tissue culture dishes in media comprising EMEM containing 0.05% LAH supplemented with 10% fetal bovine serum and the dishes incubated at 37° C. in a $CO_2$ atmosphere of 5%. After two days, the cells at approximately 80% confluence were inoculated with serial dilutions of fowl pox virus (CEVA strain) from $10^{-1}$ through $10^{-5}$ made in above media and incubated at 37° C. After 4 days, when CPE was evident, the cells were fixed to the dishes by removing the media, washing twice with 0.01 M phosphate buffered saline (PBS), pH 7.6, and fixing with IPMA fixative (35% acetone in 0.01 M PBS, pH 7.6 containing 0.02% bovine serum albumen (BSA)) for 10 minutes at room temperature. Afterwards, the fixative was removed and the fixed cells were dried in the dark at 370° C. for 90 minutes or until the fixed cells appeared visually dry. The dried fixed cells were reacted with anti-fowl pox polyclonal antiserum from chickens (obtained from SPAFAS, 190 Route 165, Preston Conn. 06365) at a 1:100 dilution in IPMA binding buffer (0.01 M PBS, pH 7.6 containing 0.05% Tween 20 (polyoxyethylene sorbitan monolaurate) and 2.95% NaCl) for one to two hours at room temperature. Afterwards, the antiserum dilutions were removed and the samples were washed three times at room temperature and at two minutes per wash with IPMA wash buffer (0.01 M PBS, pH 7.6 containing 0.05% Tween 20). Then, the samples were reacted with a 1:1000 dilution of rabbit anti-chicken IgG horseradish peroxidase conjugated antibody (Sigma Chemical Company, St. Louis, Mo.) in IPMA binding buffer for fifteen minutes at room temperature. Afterwards, the rabbit anti-chicken IgG horseradish peroxidase conjugated antibody was removed and the samples washed twice at room temperature and at two minutes per wash with IPMA wash buffer. Then, the samples were incubated in the dark for one hour at room temperature in substrate solution (0.05 M sodium acetate, pH 5.0 containing 0.012% H2O2, and 6% of a solution containing 0.33% 3-amino-9 ethylcarbazole dissolved in N, N-dimethyl formamide). Finally, the plates were drained and washed twice with water and the samples stored dried.

Figure 4A:
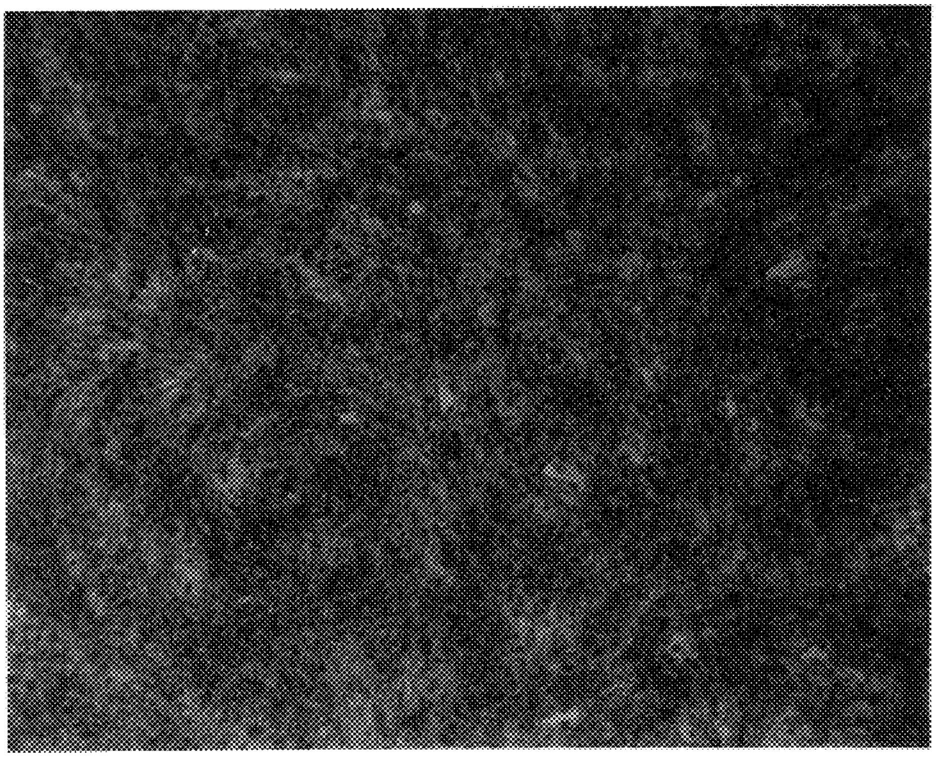
FIG. 4A is a photomicrograph of an uninfected CHCC-OU2 cells reacted with chicken anti-fowlpox virus antiserum and stained with rabbit anti-chicken IgG horseradish peroxidase conjugated antibodies.
Figure 4B:
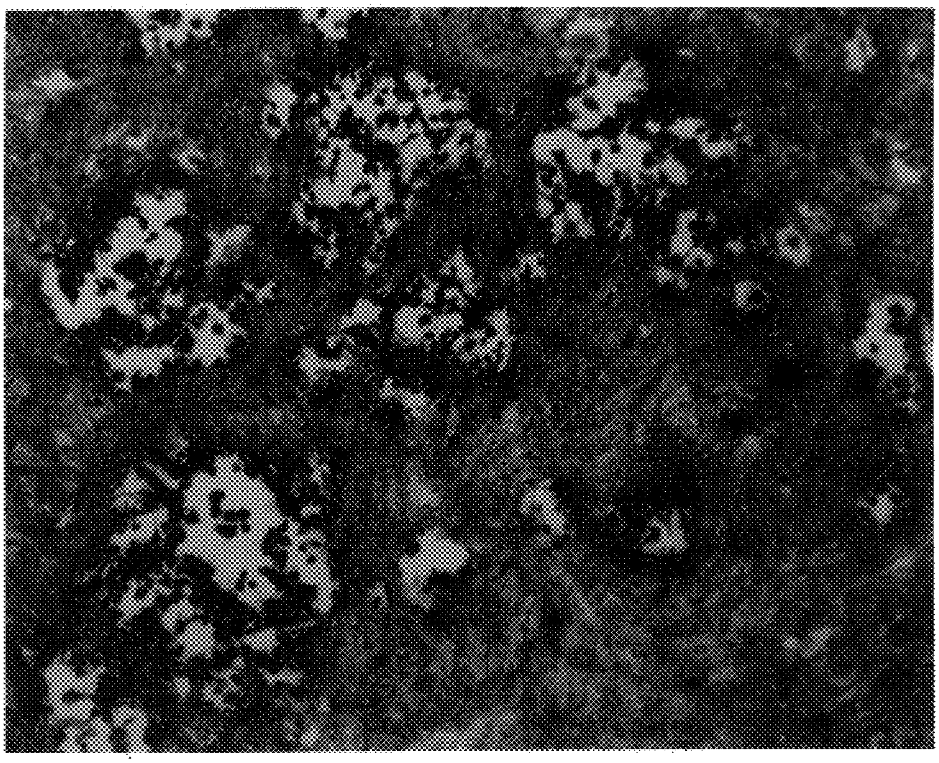
FIG. 4B is a photomicrograph of fowlpox virus infected CHCC-OU2 cells reacted with chicken anti-fowlpox virus antiserum and stained with rabbit anti-chicken IgG horseradish peroxidase conjugated antibodies.

The CHCC-OU2 cells could support the replication of fowl pox virus (FIGS. 4A and 4B) and could detect fowl pox virus diluted 1:100,000. The experiment demonstrates that the method can be used as a VI diagnostic assay. Furthermore, the experiment demonstrates that CHCC-OU2 cells can be used to prepare live virus and inactivated virus vaccines.

EXAMPLE 2

Replication of Avian Reovirus on Immortal Chicken Cell Line of the Present Invention The purpose of this experiment was to determine whether avian reovirus could replicate on CHCC-OU2 cell monolayers. While it is known that avian reovirus will replicate on primary cultures of CEF cells and poorly on several mammalian cell lines, it was unknown whether fowl pox could replicate on CHCC-OU2 cells because CHCC-OU2 cells had been chemically mutagenized which induced unknown changes in the cells that rendered the cells immortal but with a doubling time four times slower than CEF cells that could affect susceptibility of the cells to avian reovirus infection and replication. Therefore, the following experiment was performed to determine growth of avian reovirus on CHCC-OU2 cells.

Monolayers of CHCC-OU2 cells were seeded to tissue culture dishes in media comprising EMEM containing 0.05% LAH supplemented with 10% fetal bovine serum and the dishes incubated at 37° C. in a $CO_2$ atmosphere of 5%. After two days, the cells at approximately 80% confluence were inoculated with serial dilutions of reovirus (Fawley Crawley strain, reference strain from APHIS, National Veterinary Services Laboratories, P.O. Box 844, Ames Iowa 50010) from $10^{-1}$ through $10^{-5}$ made in above media and incubated at 37° C. After 4 days, when CPE was evident, the cells were fixed to the dishes by removing the media, washing twice with 0.01 M phosphate buffered saline (PBS), pH 7.6, and fixing with IPMA fixative (35% acetone in 0.01 M PBS, pH 7.6 containing 0.02% bovine serum albumen (BSA)) for 10 minutes at room temperature. Afterwards, the fixative was removed and the fixed cells were dried in the dark at 37° C. for 90 minutes or until the fixed cells appeared visually dry. The dried fixed cells were reacted with anti-reovirus polyclonal antiserum from chickens (obtained from SPAFAS, 190 Route 165, Preston Conn. 06365) at a 1:100 dilution in IPMA binding buffer (0.01 M PBS, pH 7.6 containing 0.05% Tween 20 and 2.95% NaCl) for one to two hours at room temperature. Afterwards, the antiserum dilutions were removed and the samples were washed three times at room temperature and at two minutes per wash with IPMA wash buffer (0.01 M PBS, pH 7.6 containing 0.05% Tween 20). Then, the samples were reacted with a 1:1000 dilution of rabbit anti-chicken IgG horseradish peroxidase conjugated antibody (Sigma Chemical Company, St. Louis, Mo.) in IPMA binding buffer for fifteen minutes at room temperature. Afterwards, the rabbit anti-chicken IgG horseradish peroxidase conjugated antibody was removed and the samples washed twice at room temperature and at two minutes per wash with IPMA wash buffer. Then, the samples were incubated in the dark for one hour at room temperature in substrate solution (0.05 M sodium acetate, pH 5.0 containing 0.012% H2O2, and 6% of a solution containing 0.33% 3-amino-9 ethylcarbazole dissolved in N, N-dimethyl formamide). Finally, the plates were drained and washed twice with water and the samples stored dried.

Figure 3A:
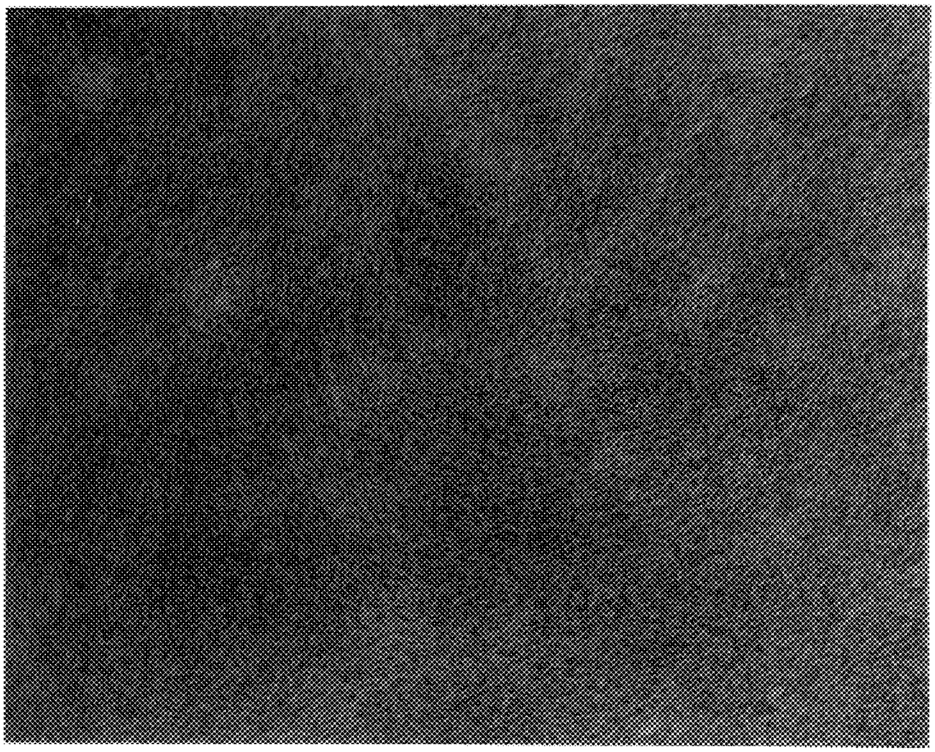
FIG. 3A is a photomicrograph of an uninfected CHCC-OU2 cells reacted with chicken anti-avian reovirus antiserum and stained with rabbit anti-chicken IgG horseradish peroxidase conjugated antibodies.
Figure 3B:
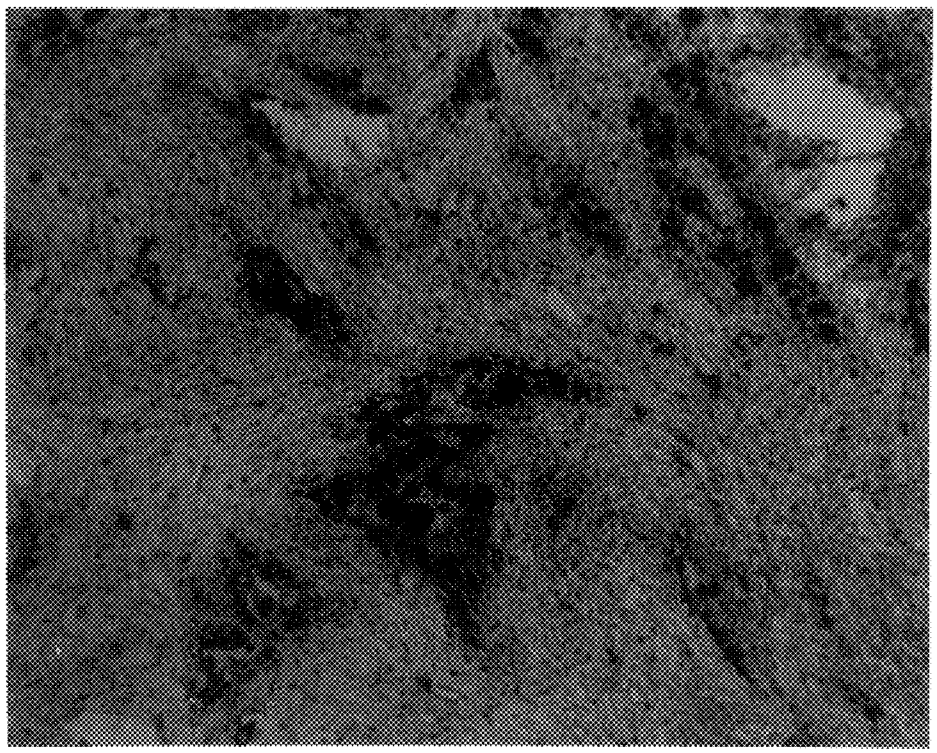
FIG. 3B is a photomicrograph of avian reovirus infected CHCC-OU2 cells reacted with chicken anti-avian reovirus antiserum and stained with rabbit anti-chicken IgG horseradish peroxidase conjugated antibodies.

The CHCC-OU2 cells could support the replication of avian reovirus (FIGS. 3A and 3B) and could detect avian reovirus diluted 1:10,000. The experiment demonstrates that the method can be used as a VI diagnostic assay. Furthermore, the experiment demonstrates that CHCC-OU2 cells can be used to prepare live virus and inactivated virus vaccines.

EXAMPLE 3

Replication of Avian Influenza Virus on Immortal Chicken Cell Line of the Present Invention The purpose of this experiment was to determine whether avian influenza virus could replicate on CHCC-OU2 cell monolayers. While it is known that avian influenza virus will replicate and develop CPE on primary cultures of CEF cells and several mammalian cell lines when the cells are overlaid with agar containing trypsin, it was unknown whether avian influenza virus could replicate on CHCC-OU2 cells because CHCC-OU2 cells had been chemically mutagenized which induced unknown changes in the cells that rendered the cells immortal but with a doubling time four times slower than CEF cells that could affect susceptibility of the cells to avian influenza virus infection, replication and the development of CPE. Therefore, the following experiment was performed to determine growth of avian influenza virus on CHCC-OU2 cells.

Monolayers of CHCC-OU2 cells were seeded to tissue culture dishes in media comprising EMEM containing 0.05% LAH supplemented with 10% fetal bovine serum and the dishes incubated at 37° C. in a $CO_2$ atmosphere of 5%. After two days, the cells at approximately 80% confluence were inoculated with serial dilutions of avian influenza virus (A/Swine/Iowa/31/H1N1 reference strain from APHIS, National Veterinary Services Laboratories, P.O. Box 844, Ames Iowa 50010) from $10^{-1}$ through $10^{-5}$ made in above media and incubated at 37° C. After 4 days, when CPE was evident, the cells were fixed to the dishes by removing the media, washing twice with 0.01 M phosphate buffered saline (PBS), pH 7.6, and fixing with IPMA fixative (35% acetone in 0.01 M PBS, pH 7.6 containing 0.02% bovine serum albumen (BSA)) for 10 minutes at room temperature. Afterwards, the fixative was removed and the fixed cells were dried in the dark at 37° C. for 90 minutes or until the fixed cells appeared visually dry. The dried fixed cells were reacted with anti-avian influenza virus polyclonal antiserum from chickens (obtained from SPAFAS, 190 Route 165, Preston Conn. 06365) at a 1:100 dilution in IPMA binding buffer (0.01 M PBS, pH 7.6 containing 0.05% Tween 20 and 2.95% NaCl) for one to two hours at room temperature. Afterwards, the antiserum dilutions were removed and the samples were washed three times at room temperature and at two minutes per wash with IPMA wash buffer (0.01 M PBS, pH 7.6 containing 0.05% Tween 20). Then, the samples were reacted with a 1:1000 dilution of rabbit anti-chicken IgG horseradish peroxidase conjugated antibody (Sigma Chemical Company, St. Louis, Mo.) in IPMA binding buffer for fifteen minutes at room temperature. Afterwards, the rabbit anti-chicken IgG horseradish peroxidase conjugated antibody was removed and the samples washed twice at room temperature and at two minutes per wash with IPMA wash buffer. Then, the samples were incubated in the dark for one hour at room temperature in substrate solution (0.05 M sodium acetate, pH 5.0 containing 0.012% H2O2, and 6% of a solution containing 0.33% 3-amino-9 ethylcarbazole dissolved in N, N-dimethyl formamide). Finally, the plates were drained and washed twice with water and the samples stored dried.

Figure 1B:
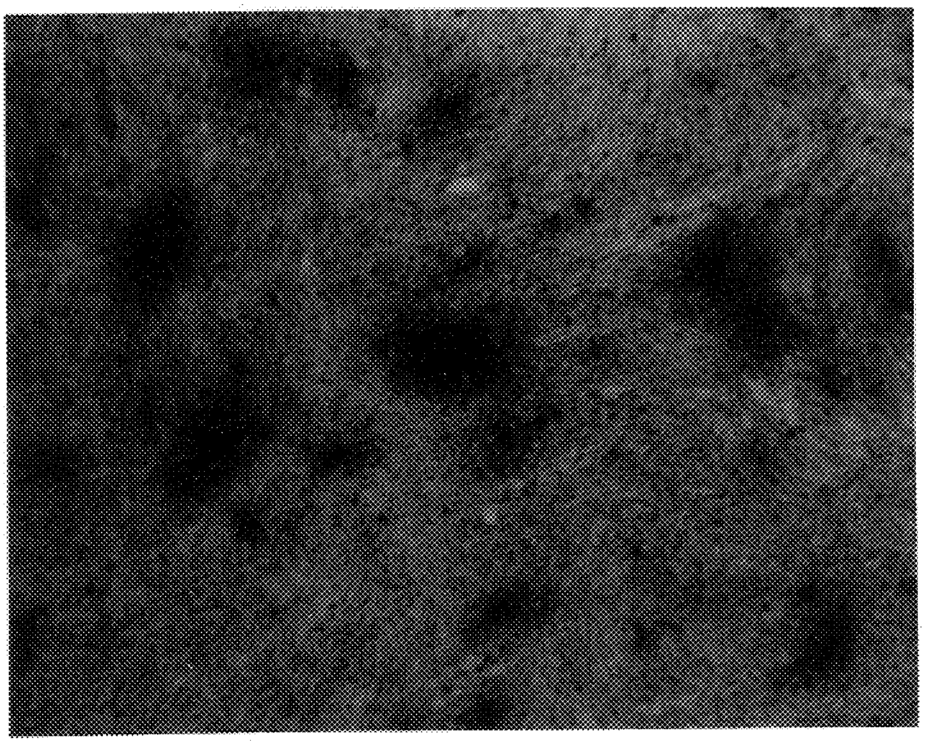
FIG. 1B is a photomicrograph of avian influenza virus infected CHCC-OU2 cells reacted with chicken anti-avian influenza virus antiserum and stained with rabbit anti-chicken IgG horseradish peroxidase conjugated antibodies.

The CHCC-OU2 cells could support the replication of avian influenza virus and development of CPE without overlaying the cells with agar containing trypsin (FIGS. 1A and 1B). Avian influenza virus diluted 1:100,000 could be detected. The experiment demonstrates that the method can be used as a VI diagnostic assay. Furthermore, the experiment demonstrates that CHCC-OU2 cells can be used to prepare live virus and inactivated virus vaccines.

EXAMPLE 4

Replication of Swine Influenza Virus on Immortal Chicken Cell Line of the Present Invention The purpose of this experiment was to determine whether swine influenza virus could replicate on CHCC-OU2 cell monolayers. While it is known that swine influenza virus will replicate and develop CPE on primary cultures of CEF cells and several mammalian cell lines when the cells are overlaid with agar containing trypsin, it was unknown whether swine influenza virus could replicate on CHCC-OU2 cells because CHCC-OU2 cells had been chemically mutagenized which induced unknown changes in the cells that rendered the cells immortal but with a doubling time four times slower than CEF cells that could affect susceptibility of the cells to swine influenza virus infection, replication and the development of CPE. Therefore, the following experiment was performed to determine growth of swine influenza virus on CHCC-OU2 cells.

Monolayers of CHCC-OU2 cells were seeded to tissue culture dishes in media comprising EMEM containing 0.05% LAH supplemented with 10% fetal bovine serum and the dishes incubated at 37° C. in a $CO_2$ atmosphere of 5%. After two days, the cells at approximately 80% confluence were inoculated with 1:5 through 1:625 serial dilutions of swine influenza virus (A/Swine/Iowa/H1N1 reference strain from APHIS, National Veterinary Services Laboratories, P.O. Box 844, Ames Iowa 50010) made in the above media and incubated at 37° C. The virus sample obtained from APHIS contained approximately 320 HA units per ml. After 4 days, when CPE was evident, the cells were fixed to the dishes by removing the media, washing twice with 0.01 M phosphate buffered saline (PBS), pH 7.6, and fixing with IPMA fixative (35% acetone in 0.01 M PBS, pH 7.6 containing 0.02% bovine serum albumen (BSA)) for 10 minutes at room temperature. Afterwards, the fixative was removed and the fixed cells were dried in the dark at 37° C. for 90 minutes or until the fixed cells appeared visually dry. The dried fixed cells were reacted with anti-swine influenza virus polyclonal antiserum from gnotobiotic pigs (obtained from National Veterinary Services Laboratories, Diagnostic Virology Laboratory, Box 844, Ames, Iowa 50010) at a 1:100 dilution in IPMA binding buffer (0.01 M PBS, pH 7.6 containing 0.05% Tween 20 and 2.95% NaCl) for one to two hours at room temperature. Afterwards, the antiserum dilutions were removed and the samples were washed three times at room temperature and at two minutes per wash with IPMA wash buffer (0.01 M PBS, pH 7.6 containing 0.05% Tween 20). Then, the samples were reacted with a 1:1000 dilution of Protein G-horseradish peroxidase in IPMA binding buffer for fifteen minutes at room temperature. Afterwards, the Protein G-horseradish peroxidase was removed and the samples were washed twice at room temperature and at two minutes per wash with IPMA wash buffer. Then, the samples were incubated in the dark for one hour at room temperature in substrate solution (0.05 M sodium acetate, pH 5.0 containing 0.012% H2O2, and 6% of a solution containing 0.33% 3-amino-9 ethylcarbazole dissolved in N, N-dimethyl formamide). Finally, the plates were drained and washed twice with water and the samples stored dried.

Figure 2A:
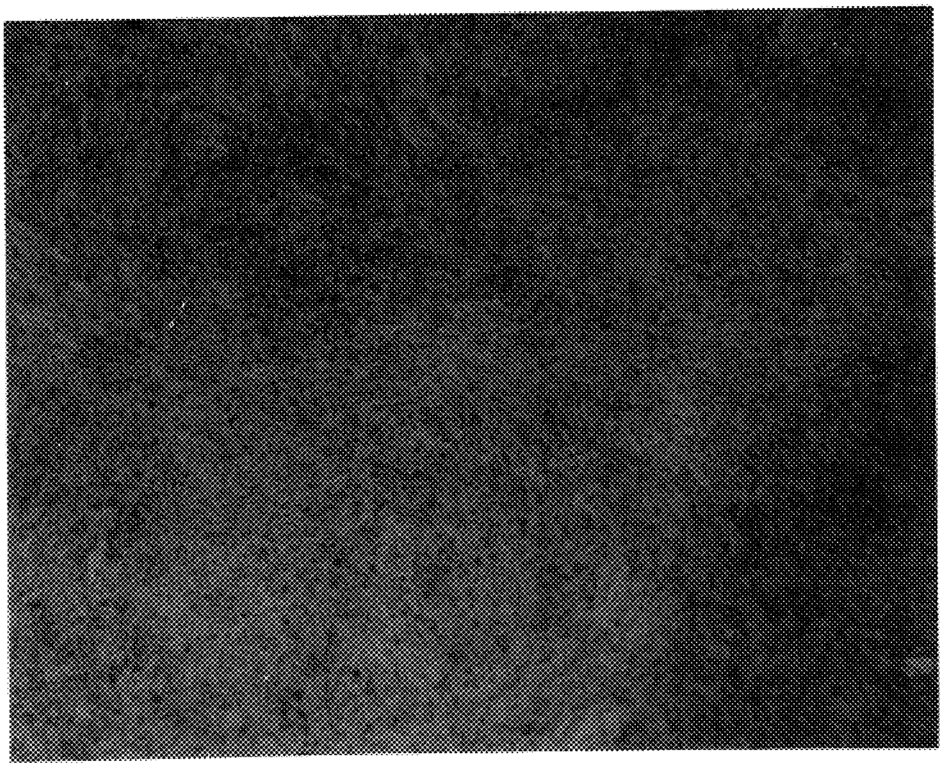
FIG. 2A is a photomicrograph of an uninfected CHCC-OU2 cells reacted with swine anti-swine influenza virus antiserum and stained with Protein G-horseradish peroxidase.
Figure 2B:
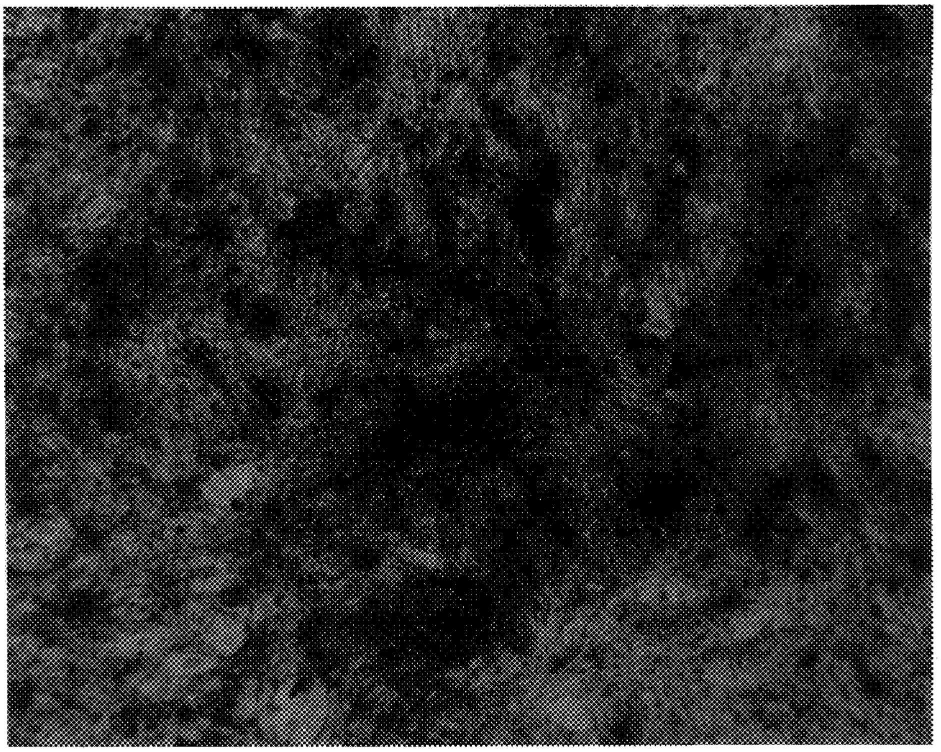
FIG. 2B is a photomicrograph of swine influenza virus infected CHCC-OU2 cells reacted with swine anti-swine influenza virus antiserum and stained with Protein G-horseradish peroxidase.

The CHCC-OU2 cells could support the replication of swine influenza virus and development of CPE (FIGS. 2A and 2B) without overlaying the cells with agar containing trypsin. Swine influenza virus at a concentration 320 HA units/ml diluted 1:625 could be detected. The experiment demonstrates that the method can be used as a VI diagnostic assay. Furthermore, the experiment demonstrates that CHCC-OU2 cells can be used to prepare live virus and inactivated virus vaccines.

EXAMPLE 5

Replication of Psittacine Herpesvirus on Immortal Chicken Cell Line of the Present Invention The purpose of this experiment was to determine whether psittacine herpesvirus could replicate on CHCC-OU2 cell monolayers. While it is known that psittacine will replicate and develop CPE on primary cultures of CEF cells, it was unknown whether psittacine herpesvirus could replicate on CHCC-OU2 cells because CHCC-OU2 cells had been chemically mutagenized which induced unknown changes in the cells that rendered the cells immortal but with a doubling time four times slower than CEF cells that could affect susceptibility of the cells to psittacine herpesvirus infection, replication and the development of CPE. Therefore, the following experiment was performed to determine growth of psittacine herpesvirus on CHCC-OU2 cells.

Monolayers of CHCC-OU2 cells were seeded to tissue culture dishes in media comprising EMEM containing 0.05% LAH supplemented with 10% fetal bovine serum and the dishes incubated at 370° C. in a $CO_2$ atmosphere of 5%. After two days, the cells at approximately 80% confluence were inoculated with $10^{-1}$ through $10^{-5}$ serial dilutions of psittacine herpesvirus (RSL-1 ATCC VR-915 is an example) made in the above media and incubated at 37° C. After 4 days, when CPE was evident, the cells were fixed to the dishes by removing the media, washing twice with 0.01 M phosphate buffered saline (PBS), pH 7.6, and fixing with IPMA fixative (35% acetone in 0.01 M PBS, pH 7.6 containing 0.02% bovine serum albumen (BSA)) for 10 minutes at room temperature. Afterwards, the fixative was removed and the fixed cells were dried in the dark at 37° C. for 90 minutes or until the fixed cells appeared visually dry. The dried fixed cells were reacted with anti-psittacine herpesvirus polyclonal antiserum made from chickens (obtained from National Veterinary Services Laboratories, Diagnostic Virology Laboratory, Box 844, Ames, Iowa 50010) at a 1:100 dilution in IPMA binding buffer (0.01 M PBS, pH 7.6 containing 0.05% Tween 20 and 2.95% NaCl) for one to two hours at room temperature. Afterwards, the antiserum dilutions were removed and the samples were washed three times at room temperature and at two minutes per wash with IPMA wash buffer (0.01 M PBS, pH 7.6 containing 0.05% Tween 20). Then, the samples were reacted with a 1:1000 dilution of rabbit anti-chicken IgG horseradish peroxidase conjugated antibody in IPMA binding buffer for fifteen minutes at room temperature. Afterwards, the rabbit anti-chicken IgG horseradish peroxidase conjugated antibody was removed and the samples were washed twice at room temperature and at two minutes per wash with IPMA wash buffer. Then, the samples were incubated in the dark for one hour at room temperature in substrate solution (0.05 M sodium acetate, pH 5.0 containing 0.012% H2O2, and 6% of a solution containing 0.33% 3-amino-9 ethylcarbazole dissolved in N, N-dimethyl formamide). Finally, the plates were drained and washed twice with water and the samples stored dried.

Figure 6A:
FIG. 6A is a photograph of an uninfected CHCC-OU2 cells reacted with chicken anti-Pachecco's herpesvirus antiserum and stained with rabbit anti-chicken IgG horseradish peroxidase conjugated antibodies.
Figure 6B:
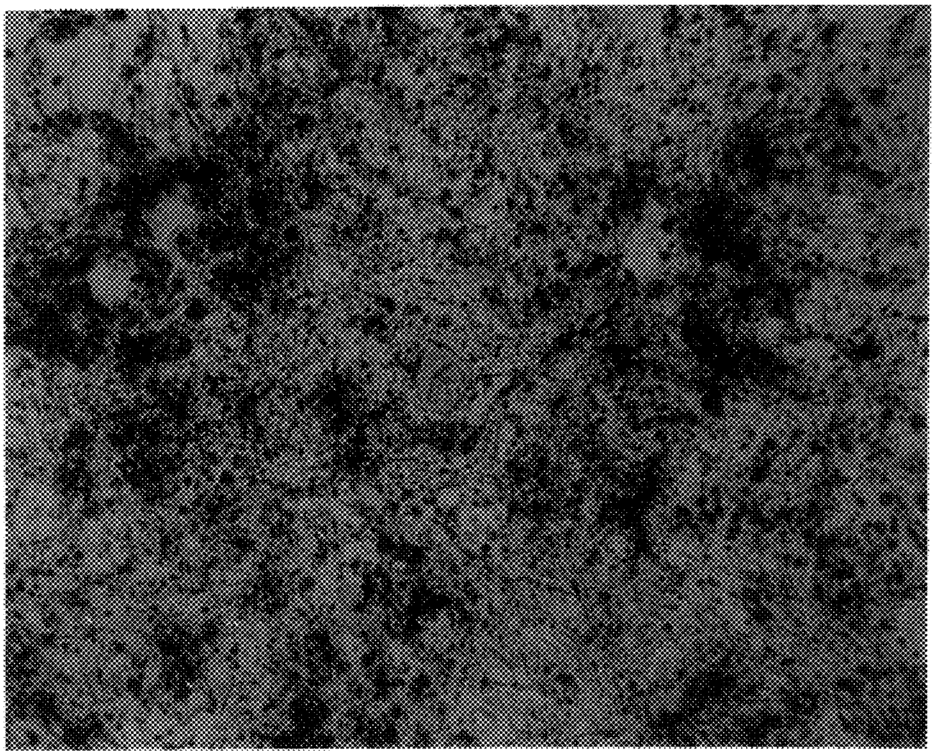
FIG. 6B is a photomicrograph of Pachecco's herpesvirus infected CHCC-OU2 cells reacted with chicken anti-Pachecco's herpesvirus antiserum and stained with rabbit anti-chicken IgG horseradish peroxidase conjugated antibodies.

The CHCC-OU2 cells could support the replication of psittacine herpesvirus and development of CPE (FIGS. 6A and 6B). Psittacine herpesvirus at a dilution of $10^{-4}$ could be detected. The experiment demonstrates that the method can be used as a VI diagnostic assay. Furthermore, the experiment demonstrates that CHCC-OU2 cells can be used to prepare live virus and inactivated virus vaccines.

EXAMPLE 6

Replication of Newcastle Disease Virus on Immortal Chicken Cell Line of the Present Invention The purpose of this experiment was to determine whether Newcastle disease virus could replicate on CHCC-OU2 cell monolayers. While it is known that Newcastle disease virus will replicate and develop CPE on CHCC-OU2 (Ogura and Fujiwara, ibid), the method for infecting CHCC-OU2 was not disclosed. It is well known that Newcastle disease virus replication on CEF cells is restricted to mesogenic and velogenic forms unless the infected cells are overlaid with agar containing $Mg^{++}$ ions and trypsin. It is also known that Newcastle disease virus can replicate on a variety of non avian cells, however replication on these cells is poor. Therefore, the following experiment was performed to determine growth of a lentogenic form of Newcastle disease virus on CHCC-OU2 cells without an agar overlay containing $Mg^{++}$ ions and trypsin.

Monolayers of CHCC-OU2 cells were seeded to tissue culture dishes in media comprising EMEM containing 0.05% LAH supplemented with 10% fetal bovine serum and the dishes incubated at 37° C. in a $CO_2$ atmosphere of 5%. After two days, the cells at approximately 80% confluence were inoculated with $10^{-1}$ through $10^{-5}$ serial dilutions of Newcastle disease virus (New Jersey-La Sota strain at a titer of $10^{9.63}$ $EID_{50}$/ml was obtained from APHIS, National Veterinary Services Laboratories, P.O. Box 844, Ames, Iowa 50010) made in the above media and incubated at 37° C. After 4 days, when CPE was evident, the cells were fixed to the dishes by removing the media, washing twice with 0.01 M phosphate buffered saline (PBS), pH 7.6, and fixing with IPMA fixative (35% acetone in 0.01 M PBS, pH 7.6 containing 0.02% bovine serum albumen (BSA)) for 10 minutes at room temperature. Afterwards, the fixative was removed and the fixed cells were dried in the dark at 37° C. for 90 minutes or until the fixed cells appeared visually dry. The dried fixed cells were reacted with anti-Newcastle disease virus polyclonal antiserum made from chickens (obtained from SPAFAS, 190 Route 165, Preston, Conn. 06365) at a 1:100 dilution in IPMA binding buffer (0.01 M PBS, pH 7.6 containing 0.05% Tween 20 and 2.95% NaCl) for one to two hours at room temperature. Afterwards, the antiserum dilutions were removed and the samples were washed three times at room temperature and at two minutes per wash with IPMA wash buffer (0.01 M PBS, pH 7.6 containing 0.05% Tween 20). Then, the samples were reacted with a 1:1000 dilution of rabbit anti-chicken IgG horseradish peroxidase conjugated antibody (Sigma Chemical Company, St. Louis, Mo.) in IPMA binding buffer for fifteen minutes at room temperature. Afterwards, the rabbit anti-chicken IgG horseradish peroxidase conjugated antibody was removed and the samples were washed twice at room temperature and at two minutes per wash with IPMA wash buffer. Then, the samples were incubated in the dark for one hour at room temperature in substrate solution (0.05 M sodium acetate, pH 5.0 containing 0.012% H2O2, and 6% of a solution containing 0.33% 3-amino-9 ethylcarbazole dissolved in N, N-dimethyl formamide). Finally, the plates were drained and washed twice with water and the samples stored dried.

Figure 5A:
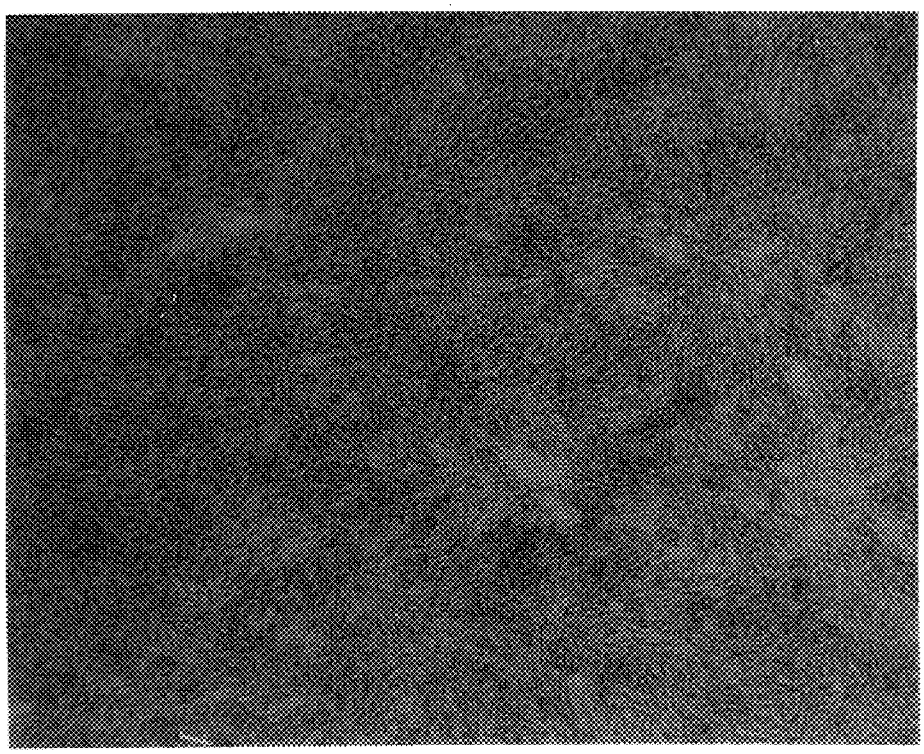
FIG. 5A is a photomicrograph of an uninfected CHCC-OU2 cells reacted with chicken anti-Newcastle disease virus antiserum and stained with rabbit anti-chicken IgG horseradish peroxidase conjugated antibodies.
Figure 5B:
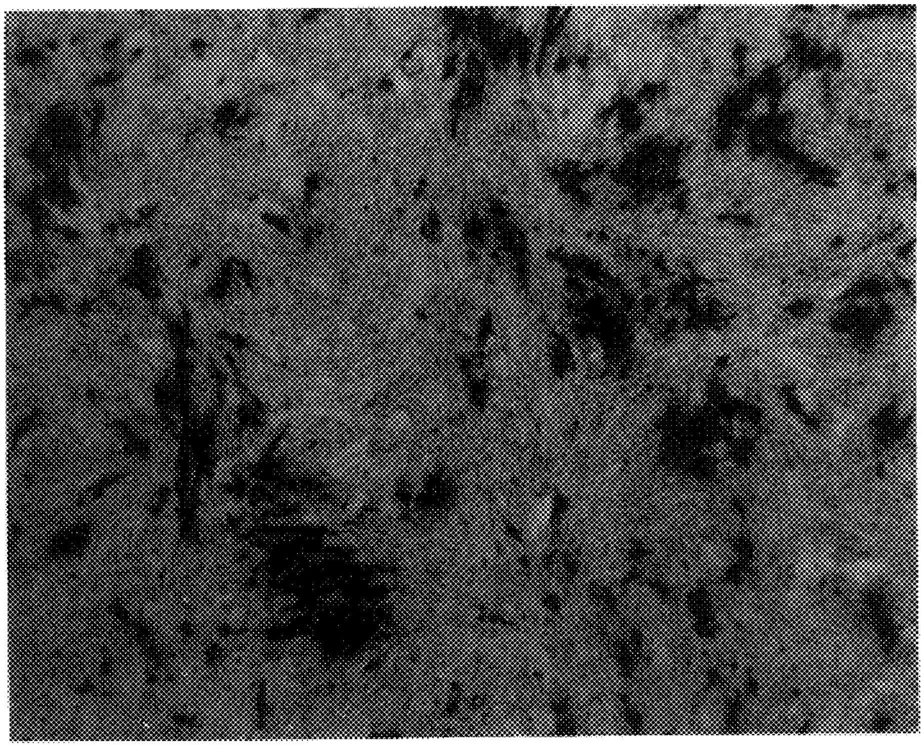
FIG. 5B is a photomicrograph of Newcastle virus infected CHCC-OU2 cells reacted with chicken anti-Newcastle disease virus antiserum and stained with rabbit anti-chicken IgG horseradish peroxidase conjugated antibodies.

The CHCC-OU2 cells could support the replication of lentogenic Newcastle disease virus and development of CPE (FIGS. 5A and 5B). Newcastle disease virus at a dilution of $10^{-5}$ could be detected. The experiment demonstrates that the method can be used as a VI diagnostic assay. Furthermore, the experiment demonstrates that CHCC-OU2 cells can be used to prepare live virus and inactivated virus vaccines.

EXAMPLE 7

Replication of Pigeon Pox Virus on Immortal Chicken Cell Line of the Present Invention The purpose of this experiment is to determine whether pigeon pox virus can replicate on CHCC-OU2 cell monolayers. It is unknown whether pigeon pox virus can replicate on CHCC-OU2 cells because CHCC-OU2 cells had been chemically mutagenized which induced unknown changes in the cells that rendered the cells immortal but with a doubling time four times slower than CEF cells that could affect susceptibility of the cells to pigeon pox virus infection and replication. Therefore, the following experiment is performed to determine whether pigeon pox virus can replicate on CHCC-OU2 cells.

Monolayers of CHCC-OU2 cells are seeded to tissue culture dishes in media comprising EMEM containing 0.05% LAH supplemented with 10% fetal bovine serum and the dishes incubated at 37° C. in a $CO_2$ atmosphere of 5%. After two days, the cells at approximately 80% confluence are inoculated with serial dilutions of pigeon pox virus from $10^{-1}$ through $10^{-5}$ made in above media and incubated at 37° C. After 4 days, when CPE is evident, the cells are fixed to the dishes by removing the media, washing twice with 0.01 M phosphate buffered saline (PBS), pH 7.6, and fixing with IPMA fixative (35% acetone in 0.01 M PBS, pH 7.6 containing 0.02% bovine serum albumen (BSA)) for 10 minutes at room temperature. Afterwards, the fixative is removed and the fixed cells are dried in the dark at 37° C. for 90 minutes or until the fixed cells appear visually dry. The dried fixed cells are reacted with chicken anti-pigeon pox polyclonal antiserum in IPMA binding buffer (0.01 M PBS, pH 7.6 containing 0.05% Tween 20 (polyoxyethylene sorbitan monolaurate) and 2.95% NaCl) for one to two hours at room temperature. Afterwards, the antiserum dilutions are removed and the samples are washed three times at room temperature and at two minutes per wash with IPMA wash buffer (0.01 M PBS, pH 7.6 containing 0.05% Tween 20). Then, the samples are reacted with a 1:1000 dilution of rabbit anti-chicken IgG horseradish peroxidase conjugated antibody (Sigma Chemical Company, St. Louis, Mo.) in IPMA binding buffer for fifteen minutes at room temperature. Afterwards, the rabbit anti-chicken IgG horseradish peroxidase conjugated antibody is removed and the samples washed twice at room temperature and at two minutes per wash with IPMA wash buffer. Then, the samples are incubated in the dark for one hour at room temperature in substrate solution (0.05 M sodium acetate, pH 5.0 containing 0.012% H2O2, and 6% of a solution containing 0.33% 3-amino-9 ethylcarbazole dissolved in N, N-dimethyl formamide). Finally, the plates are drained and washed twice with water and the samples stored dried.

The experiment demonstrates that the method can be used as a VI diagnostic assay. Furthermore, the experiment demonstrates that CHCC-OU2 cells can be used to prepare live virus and inactivated virus vaccines.

EXAMPLE 8

Replication of Canary Pox Virus on Immortal Chicken Cell Line of the Present Invention The purpose of this experiment is to determine whether canary pox virus can replicate on CHCC-OU2 cell monolayers. While it is known that canary pox viruses will replicate on primary cultures of CEF cells, it is unknown whether pigeon pox virus can replicate on CHCC-OU2 cells because CHCC-OU2 cells had been chemically mutagenized which induced unknown changes in the cells that rendered the cells immortal but with a doubling time four times slower than CEF cells that could affect susceptibility of the cells to canary pox virus infection and replication. Therefore, the following experiment is performed to determine whether canary pox virus can replicate on CHCC-OU2 cells.

Monolayers of CHCC-OU2 cells are seeded to tissue culture dishes in media comprising EMEM containing 0.05% LAH supplemented with 10% fetal bovine serum and the dishes incubated at 37° C. in a $CO_2$ atmosphere of 5%. After two days, the cells at approximately 80% confluence are inoculated with serial dilutions of canary pox virus from $10^{-1}$ through $10^{-5}$ made in above media and incubated at 37° C. After 4 days, when CPE is evident, the cells are fixed to the dishes by removing the media, washing twice with 0.01 M phosphate buffered saline (PBS), pH 7.6, and fixing with IPMA fixative (35% acetone in 0.01 M PBS, pH 7.6 containing 0.02% bovine serum albumen (BSA)) for 10 minutes at room temperature. Afterwards, the fixative is removed and the fixed cells are dried in the dark at 37° C. for 90 minutes or until the fixed cells appear visually dry. The dried fixed cells are reacted with chicken anti-canary pox polyclonal antiserum in IPMA binding buffer (0.01 M PBS, pH 7.6 containing 0.05% Tween 20 (polyoxyethylene sorbitan monolaurate) and 2.95% NaCl) for one to two hours at room temperature. Afterwards, the antiserum dilutions are removed and the samples are washed three times at room temperature and at two minutes per wash with IPMA wash buffer (0.01 M PBS, pH 7.6 containing 0.05% Tween 20). Then, the samples are reacted with a 1:1000 dilution of rabbit anti-chicken IgG horseradish peroxidase conjugated antibody (Sigma Chemical Company, St. Louis, Mo.) in IPMA binding buffer for fifteen minutes at room temperature. Afterwards, the rabbit anti-chicken IgG horseradish peroxidase conjugated antibody is removed and the samples washed twice at room temperature and at two minutes per wash with IPMA wash buffer. Then, the samples are incubated in the dark for one hour at room temperature in substrate solution (0.05 M sodium acetate, pH 5.0 containing 0.012% H2O2, and 6% of a solution containing 0.33% 3-amino-9 ethylcarbazole dissolved in N, N-dimethyl formamide). Finally, the plates are drained and washed twice with water and the samples stored dried.

The experiment demonstrates that the method can be used as a VI diagnostic assay. Furthermore, the experiment demonstrates that CHCC-OU2 cells can be used to prepare live virus and inactivated virus vaccines.

EXAMPLE 9

Replication of Quail Pox Virus on Immortal Chicken Cell Line of the Present Invention The purpose of this experiment is to determine whether quail pox virus can replicate on CHCC-OU2 cell monolayers. It is unknown whether pigeon pox virus can replicate on CHCC-OU2 cells because CHCC-OU2 cells had been chemically mutagenized which induced unknown changes in the cells that rendered the cells immortal but with a doubling time four times slower than CEF cells that could affect susceptibility of the cells to quail pox virus infection and replication. Therefore, the following experiment is performed to determine whether quail pox virus can replicate on CHCC-OU2 cells.

Monolayers of CHCC-OU2 cells are seeded to tissue culture dishes in media comprising EMEM containing 0.05% LAH supplemented with 10% fetal bovine serum and the dishes incubated at 37° C. in a $CO_2$ atmosphere of 5%. After two days, the cells at approximately 80% confluence are inoculated with serial dilutions of quail pox virus from $10^{-1}$ through $10^{-5}$ made in above media and incubated at 37° C. After 4 days, when CPE is evident, the cells are fixed to the dishes by removing the media, washing twice with 0.01 M phosphate buffered saline (PBS), pH 7.6, and fixing with IPMA fixative (35% acetone in 0.01 M PBS, pH 7.6 containing 0.02% bovine serum albumen (BSA)) for 10 minutes at room temperature. Afterwards, the fixative is removed and the fixed cells are dried in the dark at 37° C. for 90 minutes or until the fixed cells appear visually dry. The dried fixed cells are reacted with chicken antiquail pox polyclonal antiserum in IPMA binding buffer (0.01 M PBS, pH 7.6 containing 0.05% Tween 20 (polyoxyethylene sorbitan monolaurate) and 2.95% NaCl) for one to two hours at room temperature. Afterwards, the antiserum dilutions are removed and the samples are washed three times at room temperature and at two minutes per wash with IPMA wash buffer (0.01 M PBS, pH 7.6 containing 0.05% Tween 20). Then, the samples are reacted with a 1:1000 dilution of rabbit anti-chicken IgG horseradish peroxidase conjugated antibody (Sigma Chemical Company, St. Louis, Mo.) in IPMA binding buffer for fifteen minutes at room temperature. Afterwards, the rabbit anti-chicken IgG horseradish peroxidase conjugated antibody is removed and the samples washed twice at room temperature and at two minutes per wash with IPMA wash buffer. Then, the samples are incubated in the dark for one hour at room temperature in substrate solution (0.05 M sodium acetate, pH 5.0 containing 0.012% H2O2, and 6% of a solution containing 0.33% 3-amino-9 ethylcarbazole dissolved in N, N-dimethyl formamide). Finally, the plates are drained and washed twice with water and the samples stored dried.

The experiment demonstrates that the method can be used as a VI diagnostic assay. Furthermore, the experiment demonstrates that CHCC-OU2 cells can be used to prepare live virus and inactivated virus vaccines.

EXAMPLE 10

Replication of Pigeon Herpesvirus on Immortal Chicken Cell Line of the Present Invention The purpose of this experiment is to determine whether pigeon herpesvirus can replicate on CHCC-OU2 cell monolayers. It is unknown whether pigeon herpesvirus can replicate on CHCC-OU2 cells because CHCC-OU2 cells had been chemically mutagenized which induced unknown changes in the cells that rendered the cells immortal but with a doubling time four times slower than CEF cells that could affect susceptibility of the cells to pigeon herpesvirus infection, replication and the development of CPE. Therefore, the following experiment is performed to determine growth of pigeon herpesvirus on CHCC-OU2 cells.

Monolayers of CHCC-OU2 cells are seeded to tissue culture dishes in media comprising EMEM containing 0.05% LAH supplemented with 10% fetal bovine serum and the dishes incubated at 37° C. in a $CO_2$ atmosphere of 5%. After two days, the cells at approximately 80% confluence are inoculated with $10^{-1}$ through $10^{-5}$ serial dilutions of pigeon herpesvirus (B17 ATCC VR-705 is an example) made in the above media and incubated at 37° C. After 4 days, when CPE is evident, the cells are fixed to the dishes by removing the media, washing twice with 0.01 M phosphate buffered saline (PBS), pH 7.6, and fixing with IPMA fixative (35% acetone in 0.01 M PBS, pH 7.6 containing 0.02% bovine serum albumen (BSA)) for 10 minutes at room temperature. Afterwards, the fixative is removed and the fixed cells are dried in the dark at 37° C. for 90 minutes or until the fixed cells appear visually dry. The dried fixed cells are reacted with chicken anti-pigeon herpesvirus polyclonal antiserum at in IPMA binding buffer (0.01 M PBS, pH 7.6 containing 0.05% Tween 20 and 2.95% NaCl) for one to two hours at room temperature. Afterwards, the antiserum dilutions are removed and the samples are washed three times at room temperature and at two minutes per wash with IPMA wash buffer (0.01 M PBS, pH 7.6 containing 0.05%

Tween 20). Then, the samples are reacted with a 1:1000 dilution of rabbit anti-chicken IgG horseradish peroxidase conjugated antibody in IPMA, binding buffer for fifteen minutes at room temperature. Afterwards, the rabbit anti-chicken IgG horseradish peroxidase conjugated antibody peroxidase is removed and the samples are washed twice at room temperature and at two minutes per wash with IPMA wash buffer. Then, the samples are incubated in the dark for one hour at room temperature in substrate solution (0.05 M sodium acetate, pH 5.0 containing 0.012% H2O2, and 6% of a solution containing 0.33% 3-amino-9 ethylcarbazole dissolved in N, N-dimethyl formamide). Finally, the plates are drained and washed twice with water and the samples are stored dried.

The experiment demonstrates that the method can be used as a VI diagnostic assay. Furthermore, the experiment demonstrates that CHCC-OU2 cells can be used to prepare live virus and inactivated virus vaccines.

EXAMPLE 11

Replication of Falcon Herpesvirus on Immortal Chicken Cell Line of the Present Invention The purpose of this experiment is to determine whether falcon herpesvirus can replicate on CHCC-OU2 cell monolayers. It is unknown whether falcon herpesvirus can replicate on CHCC-OU2 cells because CHCC-OU2 cells had been chemically mutagenized which induced unknown changes in the cells that rendered the cells immortal but with a doubling time four times slower than CEF cells that could affect susceptibility of the cells to falcon herpesvirus infection, replication and the development of CPE. Therefore, the following experiment is performed to determine growth of falcon herpesvirus on CHCC-OU2 cells.

Monolayers of CHCC-OU2 cells are seeded to tissue culture dishes in media comprising EMEM containing 0.05% LAH supplemented with 10% fetal bovine serum and the dishes incubated at 37° C. in a $CO_2$ atmosphere of 5%. After two days, the cells at approximately 80% confluence are inoculated with $10^{-1}$ through $10^{-5}$ serial dilutions of falcon herpesvirus (S-18 ATCC VR-709 is an example) made in the above media and incubated at 37° C. After 4 days, when CPE is evident, the cells are fixed to the dishes by removing the media, washing twice with 0.01 M phosphate buffered saline (PBS), pH 7.6, and fixing with IPMA fixative (35% acetone in 0.01 M PBS, pH 7.6 containing 0.02% bovine serum albumen (BSA)) for 10 minutes at room temperature. Afterwards, the fixative is removed and the fixed cells are dried in the dark at 37° C. for 90 minutes or until the fixed cells appear visually dry. The dried fixed cells are reacted with chicken anti-falcon herpesvirus polyclonal antiserum at in IPMA binding buffer (0.01 M PBS, pH 7.6 containing 0.05% TWEEN 20 and 2.95% NaCl) for one to two hours at room temperature. Afterwards, the antiserum dilutions are removed and the samples are washed three times at room temperature and at two minutes per wash with IPMA wash buffer (0.01 M PBS, pH 7.6 containing 0.05% Tween 20). Then, the samples are reacted with a 1:1000 dilution of rabbit anti-chicken IgG horseradish peroxidase conjugated antibody in IPMA binding buffer for fifteen minutes at room temperature. Afterwards, the rabbit anti-chicken IgG horseradish peroxidase conjugated antibody is removed and the samples are washed twice at room temperature and at two minutes per wash with IPMA wash buffer. Then, the samples are incubated in the dark for one hour at room temperature in substrate solution (0.05 M sodium acetate, pH 5.0 containing 0.012% H2O2, and 6% of a solution containing 0.33% 3-amino-9 ethylcarbazole dissolved in N, N-dimethyl formamide). Finally, the plates are drained and washed twice with water and the samples are stored dried.

The experiment demonstrates that the method can be used as a VI diagnostic assay. Furthermore, the experiment demonstrates that CHCC-OU2 cells can be used to prepare live virus and inactivated virus vaccines.

EXAMPLE 12

Replication of Infectious Bursal Disease Virus on Immortal Chicken Cell Line of the Present Invention The purpose of this experiment is to determine whether vaccine strains of infectious bursal disease virus adapted to replicate on primary cultures of CEF cells can replicate on CHCC-OU2 cell monolayers. It was unknown whether these same viruses can replicate on CHCC-OU2 cells because CHCC-OU2 cells had been chemically mutagenized which induced unknown changes in the cells that rendered the cells immortal but with a doubling time four times slower than CEF cells that could affect susceptibility of the cells to infectious bursal disease virus infection, replication and the development of CPE. We had determined that a non-vaccine strain of infectious bursal disease virus replicated poorly on CHCC-OU2 cells (see table II). Therefore, the following experiment is performed to determine growth of CEF-adapted strains of infectious bursal disease virus on CHCC-OU2 cells.

Monolayers of CHCC-OU2 cells are seeded to tissue culture dishes in media comprising EMEM containing 0.05% LAH supplemented with 10% fetal bovine serum and the dishes incubated at 37° C. in a $CO_2$ atmosphere of 5%. After two days, the cells at approximately 80% confluence are inoculated with $10^{-1}$ through $10^{-5}$ serial dilutions of CEF-adapted infectious bursal disease virus Cu-1 (Nick et al. (1976). Journal of Virology, vol. 18, pp. 227–234), Cu-1M (Cursiefen et al. (1979). Archives of Virology, vol. 59, pp. 39–46), and 23/82 (Chettle et al. (1985). British Veterinary Journal, vol. 141, pp. 141–145) are examples of CEF-adapted infectious bursal disease virus strains) made in the above media and incubated at 37° C. After 4 days, when CPE is evident, the cells are fixed to the dishes by removing the media, washing twice with 0.01 M phosphate buffered saline (PBS), pH 7.6, and fixing with IPMA fixative (35% acetone in 0.01 M PBS, pH 7.6 containing 0.02% bovine serum albumen (BSA)) for 10 minutes at room temperature. Afterwards, the fixative is removed and the fixed cells are dried in the dark at 37° C. for 90 minutes or until the fixed cells appear visually dry. The dried fixed cells are reacted with chicken anti-infectious bursal disease virus polyclonal antiserum at in IPMA binding buffer (0.01 M PBS, pH 7.6 containing 0.05% TWEEN 20 and 2.95% NaCl) for one to two hours at room temperature. Afterwards, the antiserum dilutions are removed and the samples are washed three times at room temperature and at two minutes per wash with IPMA wash buffer (0.01 M PBS, pH 7.6 containing 0.05% Tween 20). Then, the samples are reacted with a 1:1000 dilution of rabbit anti-chicken IgG horseradish peroxidase conjugated antibody in IPMA binding buffer for fifteen minutes at room temperature. Afterwards, the rabbit anti-chicken IgG horseradish peroxidase conjugated antibody is removed and the samples are washed twice at room temperature and at two minutes per wash with IPMA wash buffer. Then, the samples are incubated in the dark for one hour at room temperature in substrate solution (0.05 M sodium acetate, pH 5.0 containing 0.012% H2O2, and 6% of a solution containing 0.33% 3-amino-9 ethylcarbazole dissolved in N, N-dimethyl formamide). Finally, the plates are drained and washed twice with water and the samples are stored dried.

The experiment demonstrates that CHCC-OU2 cells can be used to prepare live virus and inactivated virus vaccines from infectious bursal disease virus that had been previously adapted to replicate on CEF.

EXAMPLE 13

Replication of Avian Polvomavirus on Immortal Chicken Cell Line of the Present Invention The purpose of this experiment is to determine whether avian polyomavirus (budgerigar fledgling disease) can replicate on CHCC-OU2 cell monolayers. While it is known that avian polyomavirus can replicate on CEF cells t is unknown whether avian polyomavirus can replicate on CHCC-OU2 cells because CHCC-OU2 cells had been chemically mutagenized which induced unknown changes in the cells that rendered the cells immortal but with a doubling time four times slower than CEF cells that could affect susceptibility of the cells to avian polyomavirus infection, replication and the development of CPE. Therefore, the following experiment is performed to determine growth of falcon herpesvirus on CHCC-OU2 cells.

Monolayers of CHCC-OU2 cells are seeded to tissue culture dishes in media comprising EMEM containing 0.05% LAH supplemented with 10% fetal bovine serum and the dishes incubated at 37° C. in a $CO_2$ atmosphere of 5%. After two days, the cells at approximately 80% confluence are inoculated with $10^{-1}$ through $10^{-5}$ serial dilutions of avian polyomavirus made in the above media and incubated at 37° C. After 4 days, when CPE is evident, the cells are fixed to the dishes by removing the media, washing twice with 0.01 M phosphate buffered saline (PBS), pH 7.6, and fixing with IPMA fixative (35% acetone in 0.01 M PBS, pH 7.6 containing 0.02% bovine serum albumen (BSA)) for 10 minutes at room temperature. Afterwards, the fixative is removed and the fixed cells are dried in the dark at 37° C. for 90 minutes or until the fixed cells appear visually dry. The dried fixed cells are reacted with chicken anti-avian polyomavirus polyclonal antiserum at in IPMA binding buffer (0.01 M PBS, pH 7.6 containing 0.05% TWEEN 20 and 2.95% NaCl) for one to two hours at room temperature. Afterwards, the antiserum dilutions are removed and the samples are washed three times at room temperature and at two minutes per wash with IPMA wash buffer (0.01 M PBS, pH 7.6 containing 0.05% TWEEN 20). Then, the samples are reacted with a 1:1000 dilution of rabbit anti-chicken IgG horseradish peroxidase conjugated antibody in IPMA binding buffer for fifteen minutes at room temperature. Afterwards, the rabbit anti-chicken IgG horseradish peroxidase conjugated antibody is removed and the samples are washed twice at room temperature and at two minutes per wash with IPMA wash buffer. Then, the samples are incubated in the dark for one hour at room temperature in substrate solution (0.05 M sodium acetate, pH 5.0 containing 0.012% H2O2, and 6% of a solution containing 0.33% 3-amino-9 ethylcarbazole dissolved in N, N-dimethyl formamide). Finally, the plates are drained and washed twice with water and the samples are stored dried.

The experiment demonstrates that the method can be used as a VI diagnostic assay. Furthermore, the experiment demonstrates that CHCC-OU2 cells can be used to prepare live virus and inactivated virus vaccines.

EXAMPLE 14

Killed Vaccine Produced on Immortal Chicken Cell Line of the Present Invention The present invention is used to produce killed vaccines that are used to protect avians or animals against infection. The present invention can be practiced with any of the following viruses: avian influenza virus, avian reovirus, fowl pox virus, pigeon pox virus, canary pox virus, psittacine herpesvirus, pigeon herpesvirus, falcon herpesvirus, Newcastle disease virus, infectious bursal disease virus, infectious bronchitis virus, avian encephalomyelitis virus, chicken anemia virus, avian adenovirus type, swine influenza virus, and avian polyomavirus. The antigenic mass of any of the aforementioned viruses propagated by the present invention is used for vaccines. Once the virus is propagated to high titers, it would be readily apparent by those skilled in the art that the virus antigenic mass could be obtained by methods practiced by those skilled in the art. For example, the virus antigenic mass may be obtained by dilution, concentration, or extraction. All of these methods have been employed to obtain virus antigenic mass to produce vaccines.

The following is a description by which an inactivated vaccine is produced. The virus is grown according to the method of the present invention to a high titer. The virus is then isolated by art-known methods and inactivated by treatment with formalin or with binary ethyleneimine (BEI), both methods are well known to those skilled in the art. The aforementioned inactivated virus is mixed with any of the art-known adjuvants. The resulting vaccine formulations are administered to the avian or animal by methods familiar to those skilled in the art.

An example of inactivation by formalin is mixing the virus suspension with 37% formaldehyde to a final formaldehyde concentration of 0.05%. The virus-formaldehyde mixture is mixed by constant stirring for approximately 24 hours at room temperature. The inactivated virus mixture is tested for residual live virus by assaying for growth on M-CSF treated monocytes of the present invention.

An example of inactivation by BEI is mixing the virus suspension with 0.1 M BEI (2-bromo-ethylamine in 0.175 N NaOH) to a final BEI concentration of 1 mM. The virus-BEI mixture is mixed by constant stirring for approximately 48 hours at room temperature, followed by the addition of 1.0 M sodium thiosulphate to a final concentration of 0.1 mM. Mixing is continued for an additional two hours. The inactivated virus mixture is tested for residual live virus by assaying for growth on M-CSF treated monocytes of the present invention.

EXAMPLE 15

Live Vaccine Produced by the Immortal Chicken Cell Line of the Present Invention The present invention is used to produce live vaccines to protect avians and animals against infection. The present invention is practiced with any of the following viruses, either in an attenuated form or non-pathogenic form: avian influenza virus, avian reovirus, fowl pox virus, pigeon pox virus, canary pox virus, psittacine herpesvirus, pigeon herpesvirus, falcon herpesvirus, Newcastle disease virus, infectious bursal disease virus, infectious bronchitis virus, avian encephalomyelitis virus, chicken anemia virus, avian adenovirus type, swine influenza virus, and avian polyomavirus. Any one of the aforementioned viruses that are no longer pathogenic is propagated according to the method of the present invention to high titers. Virus prepared by the method of the present invention is concentrated, frozen, and stored at −70° C. or lower, is frozen and stored undiluted at −70° C. or lower, or lyophilized and stored at 4° C. or lower. Virus for vaccination is mixed with a saline solution to the appropriate dosage and administered either by any of the methods known to those skilled in the art.

EXAMPLE 16

Diagnostic Assay Using the Immortal Chicken Cell Line of the Present Invention

The present invention is used as a diagnostic to determine the presence of avian influenza virus, avian reovirus, fowl pox virus, pigeon pox virus, canary pox virus, psittacine herpesvirus, pigeon herpesvirus, falcon herpesvirus, Newcastle disease virus, infectious bursal disease virus, infectious bronchitis virus, avian encephalomyelitis virus, chicken anemia virus, avian adenovirus type, swine influenza virus, or avian polyomavirus in blood or tissues of animals suspected of being infected with any of the aforementioned viruses by virus isolation, serological methods or PCR. The method can use microtiter plates with the cell line of the present invention in the wells to which the tissue is added. Detection of virus is by microscopic examination. Identification of virus is by serological assays using antibodies against the virus, by hemagglutination assays wherein chicken or sheep erythrocytes are added to the wells after development of CPE, by PCR of the tissue culture fluid removed from the wells, by ELISA whereby tissue culture fluid is removed from the well and subjected to an ELISA assay, and by electron microscopy of the tissue culture fluid removed from the well.

EXAMPLE 17

Modifying Viruses in the Cell Line of the Present Invention

Several avian viruses can replicate in embryonated eggs and avian cell cultures but do not replicate either efficiently or at all in primary CEF cell cultures. Examples of these viruses are chicken anemia virus, various groups of avian adenovirus, and avian encephalomyelitis virus. Other viruses that can replicate in primary avian cell cultures or cell lines after being adapted to the cell line are infectious bursal disease virus and infectious bronchitis virus. It is well known by those skilled in the art that many viruses can be modified to replicate in a plurality of primary cell types and cell lines by infecting the cells with the virus and blind passaging the infected cells until CPE eventually appears, indicating that the virus has been modified to replicate in the cells. The number of passages before CPE becomes evident can vary but is usually within the range of 1 to 5 passages. Viruses modified in such a manner are suitable for use in inactivated vaccines. More extensive passaging in the cells can further modify the virus to include mutations that render the virus non-pathogenic or attenuated but immunogenic in the natural host of the virus. Such attenuated viruses have been used as live vaccines.

The cell line of the present invention is infected the aforementioned viruses and the infected cell line subcultured for at least one passage. The is infected cells are passaged until CPE becomes evident or presence of infectious virus, indicative of virus replication can be determined by any of the immunological methods known to those skilled in the art. It is known to those skilled in the art that not all viruses that replicate in infected cells and release infectious progeny virus form obvious CPE during infection of primary cells or cell line.

The cell line of the present infection is used to modify or attenuate any of the following viruses: avian influenza virus, avian reovirus, fowl pox virus, pigeon pox virus, canary pox virus, psittacine herpesvirus, pigeon herpesvirus, falcon herpesvirus, Newcastle disease virus, infectious bursal disease virus, infectious bronchitis virus, avian encephalomyelitis virus, chicken anemia virus, avian adenovirus, swine influenza virus, and avian polyomavirus. The modified or attenuated viruses are used as live vaccines.

The cell line of the present invention is infected the aforementioned viruses and the infected cell line subcultured for a multiplicity of passages. Virus is isolated after various passage levels and tested for pathogenicity and immunogenicity in the viruses natural host. Virus at any tested passage that is both nonpathogenic or nearly so and is immunogenic is tested for ability to protect the host against challenge with virulent virus. The aforementioned viruses modified in the instant example that are both nonpathogenic or nearly so and can protect against disease are useful as live vaccines.

EXAMPLE 18

Replication of Equine Influenza Virus on the Immortal Chicken Cell Line of the Present Invention The purpose of this experiment was to determine whether equine influenza virus could replicate on CHCC-OU2 cell monolayers. While it is known that equine influenza virus will replicate and develop CPE on primary cultures of CEF cells and several mammalian cell lines when the cells are overlaid with agar containing trypsin, it was unknown whether equine influenza virus could replicate on CHCC-OU2 cells because CHCC-OU2 cells had been chemically mutagenized which induced unknown changes in the cells that rendered the cells immortal but with a doubling time four times slower than CEF cells that could affect susceptibility of the cells to equine influenza virus infection, replication and the development of CPE. Therefore, the following experiment was performed to determine growth of equine influenza virus on CHCC-OU2 cells.

Monolayers of CHCC-OU2 cells were seeded to tissue culture dishes in media comprising EMEM containing 0.05% LAH supplemented with 10% fetal bovine serum and the dishes incubated at 37° C. in a $CO_2$ atmosphere of 5%. After two days, the cells at approximately 80% confluence were inoculated with serial dilutions of equine influenza virus (Miami strain and Prague strain from APHIS, National Veterinary Services Laboratories, P.O. Box 844, Ames Iowa 50010) from $10^{-1}$ through $10^{-5}$ made in above media and incubated at 37° C. After 4 days, the cells were fixed to the dishes by removing the media, washing twice with 0.01 M phosphate buffered saline (PBS), pH 7.6, and fixing with IPMA fixative (35% acetone in 0.01 M PBS, pH 7.6 containing 0.02% bovine serum albumen (BSA)) for 10 minutes at room temperature. Afterwards, the fixative was removed and the fixed cells were dried in the dark at 37° C. for 90 minutes or until the fixed cells appeared visually dry. The dried fixed cells were reacted with either anti-equine influenza virus Miami or anti-equine influenza virus Prague polyclonal antiserum from chickens (obtained from SPAFAS, 190 Route 165, Preston Conn. 06365) at a 1:100 dilution in IPMA binding buffer (0.01 M PBS, pH 7.6 containing 0.05% TWEEN 20 and 2.95% NaCl) for one to two hours at room temperature. Afterwards, the antiserum dilutions were removed and the samples were washed three times at room temperature and at two minutes per wash with IPMA wash buffer (0.01 M PBS, pH 7.6 containing 0.05% Tween 20). Then, the samples were reacted with a 1:1000 dilution of rabbit anti-chicken IgG horseradish peroxidase conjugated antibody (Sigma Chemical Company, St. Louis, Mo.) in IPMA binding buffer for fifteen minutes at room temperature. Afterwards, the rabbit anti-chicken IgG horseradish peroxidase conjugated antibody was removed and the samples washed twice at room temperature and at two minutes per wash with IPMA wash buffer. Then, the samples were incubated in the dark for one hour at room temperature in substrate solution (0.05 M sodium acetate, pH 5.0 containing 0.012% H2O2, and 6% of a solution containing 0.33% 3-amino-9 ethylcarbazole dissolved in N, N-dimethyl formamide). Finally, the plates were drained and washed twice with water and the samples stored dried.

Figure 7A:
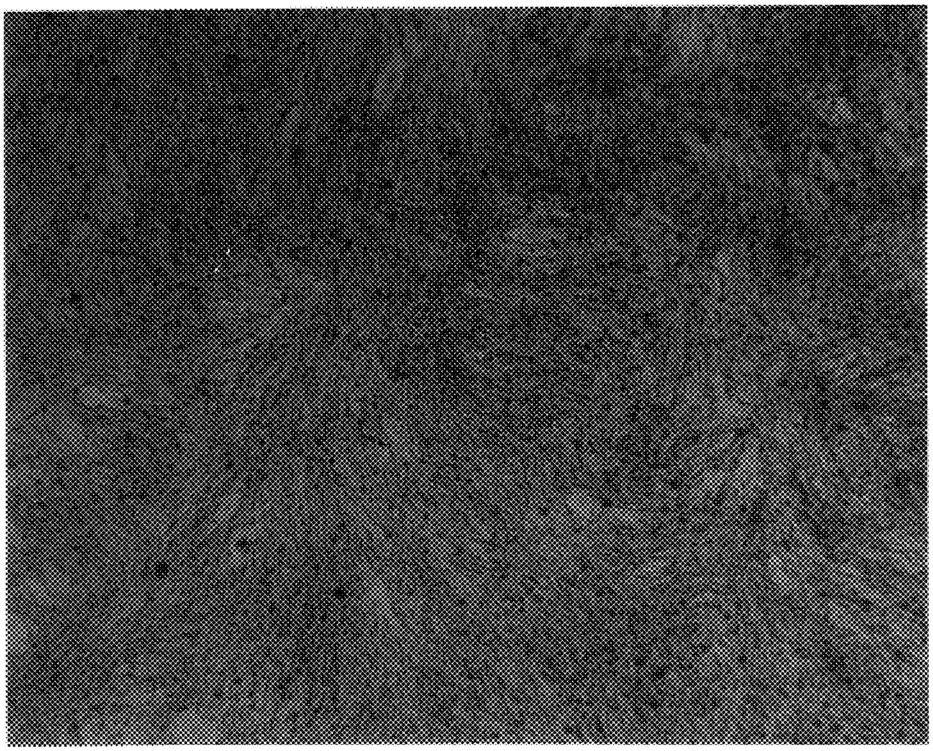
FIG. 7A is a photomicrograph of an uninfected CHCC-OU2 cells reacted with chicken anti-equine influenza virus (Miami) antiserum and stained with rabbit anti-chicken IgG horseradish peroxidase conjugated antibodies.
Figure 7B:
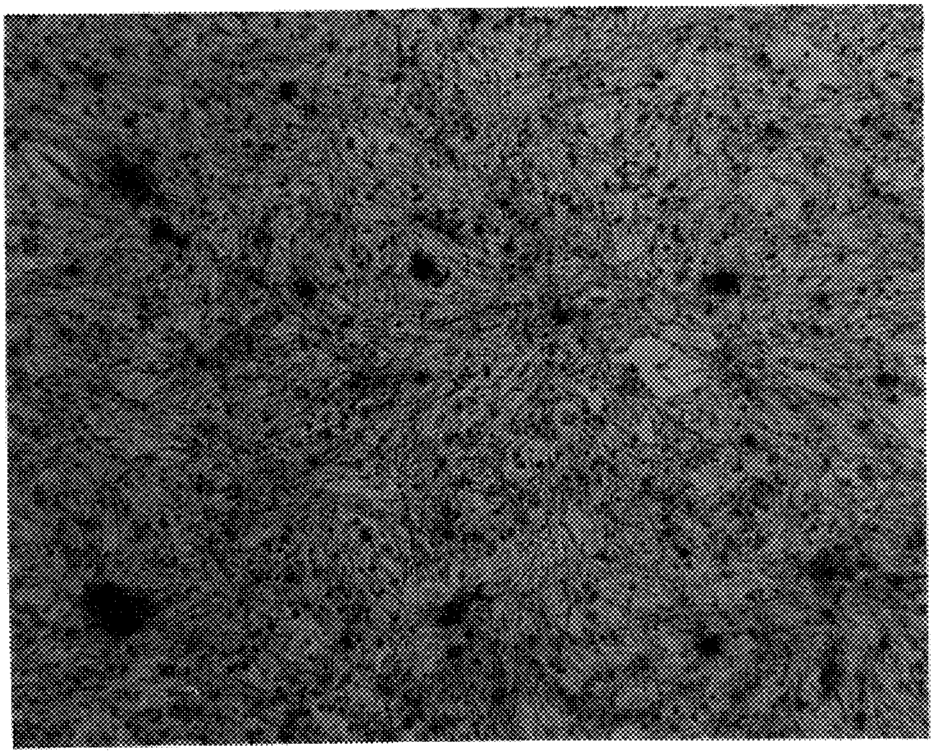
FIG. 7B is a photomicrograph of equine influenza virus (Miami) infected CHCC-OU2 cells reacted with chicken anti-equine influenza virus (Miami) antiserum and stained with rabbit anti-chicken IgG horseradish peroxidase conjugated antibodies.
Figure 8A:
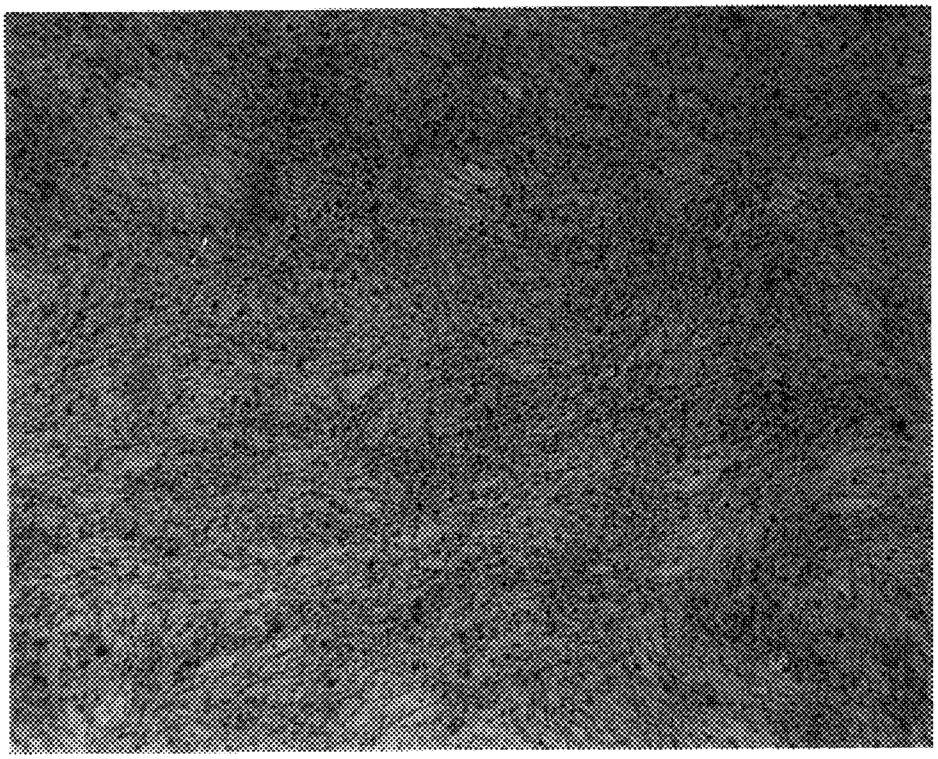
FIG. 8A is a photomicrograph of an uninfected CHCC-OU2 cells reacted with chicken anti-equine influenza virus (Prague) antiserum and stained with rabbit anti-chicken IgG horseradish peroxidase conjugated antibodies.
Figure 8B:
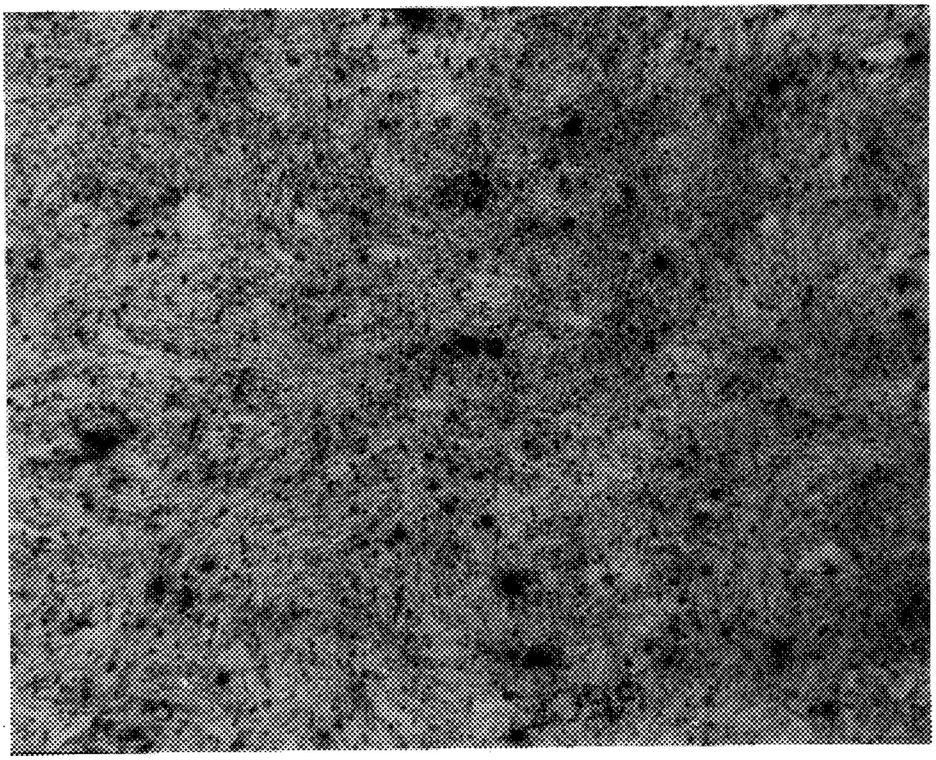
FIG. 8B is a photomicrograph of equine influenza virus (Prague) infected CHCC-OU2 cells reacted with chicken anti-equine influenza virus (Prague) antiserum and stained with rabbit anti-chicken IgG horseradish peroxidase conjugated antibodies.

The CHCC-OU2 cells could support the replication of avian influenza virus Miami (FIGS. 7A and 7B) and Prague (FIGS. 8A and 8B), however without overlaying the cells with agar containing trypsin the virus appeared not to be able to spread readily. The experiment demonstrates that the method can be used as a VI diagnostic assay, however for virus spread and CPE the infected cells need to be overlaid with agar containing trypsin. Using agar overlays containing trypsin to propagate influenza viruses in cell culture is known to those skilled in the art (K. K. Brown and R. C. Stewart, U.S. Pat. No. RE. 33,164).

The method of the present invention can be used to produce vaccines for humans and lower mammals. The method of the present invention is unique in its broad applications to many different virus.

It is intended that the foregoing descriptions be only illustrative of the present invention and that the present invention be limited only by the hereinafter appended claims.

We claim:

1. An avian vaccine, comprising: an immortal chicken embryo cell line infected with a vaccine strain of Marek's disease virus, wherein the vaccine induces a protective immune response when administered to an avian.

2. The avian vaccine according to claim 1, wherein the cell line is derived from chicken embryo cells that had been treated with a chemical mutagen to render the immortal cell line.

3. The avian vaccine according to claim 2, wherein the cell line comprises CHCC-OU2 cells deposited as ATCC CRL 12302.

4. The avian vaccine of claim 2, wherein the chemical mutagen is MNNG.

5. A method for propagating an avian virus, comprising: (a) providing a cell line generated from chicken embryo cells that have been treated with a chemical mutagen to create an immortal cell line said cell line being virus free; (b) infecting said immortal cell line with an avian virus selected from the group of virus families consisting of Adenoviradae, Birnaviradae, Coronaviradae, Herpesviradae Orthomyxoviradae, Picornaviradae, Poxviradae, Reoviradae, and Polyomaviradae; (c) cultivating the infected immortal cell line to produce the immortal cell line infected with the avian virus; and (d) removing the virus from the immortal cell line.

6. The method according to claim 5, wherein the chemical mutagen is MNNG.

7. The method according to claim 5, wherein the cell line comprises CHCC-OU2 cells deposited as ATCC CRL 12302.

8. The method according to claim 5, wherein the avian virus is selected from the group consisting of avian influenza virus, avian reovirus, fowl pox virus, pigeon pox virus, canary pox virus, psittacine herpesvirus, pigeon herpesvirus, falcon herpesvirus, infectious bursal disease virus, infectious bronchitis virus, avian encephalomyelitis virus, chicken anemia virus, avian adenovirus, and avian polyomavirus.

9. A method for providing an avian vaccine, comprising: (a) providing a cell line generated from chicken embryo cells that have been treated with a chemical mutagen to create an immortal cell line; (b) infecting said cell line with a virus; (c) cultivating said infected cell line to produce the virus; (d) harvesting the virus from the cultivated cell line; and (e) subjecting the harvested virus to at least one of the following treatments: (i) inactivating the virus, (ii) adding a pharmaceutically acceptable carrier or diluent, (iii) adding an adjuvant, (iv) adding a stabilizer, (v) lyophilizing, wherein the vaccine induces protective immunity in avians.

10. The method according to claim 9, wherein the chemical mutagen is MNNG.

11. The method according to claim 9, wherein the cell line comprises CHCC-OU2 deposited as ATCC CRL 12302.

12. A method for propagating swine influenza virus, comprising: (a) providing a cell line generated from chicken embryo cells that have been treated with a chemical mutagen to create an immortal cell line said cell line being virus free; (b) infecting said cell line with swine influenza virus; (c) cultivating the infected cell line to produce the swine influenza virus; and removing the virus from the cell line.

13. The method according to claim 12, wherein the chemical mutagen is MNNG.

14. The method according to claim 12, wherein the cell line comprises CHCC-OU2 cells deposited as ATCC CRL 12302.

15. A method for preparing a swine influenza vaccine, comprising: (a) providing a cell line generated from chicken embryo cells that have been treated with a chemical mutagen to create an immortal cell line; (b) infecting said cell line with the virus; (c) cultivating said infected cell line to produce the virus; (d) harvesting the virus from the cultivated cell line; and (e) subjecting the harvested virus to at least one of the following treatments: (i) inactivating the virus, (ii) adding a pharmaceutically acceptable carrier or diluent, (iii) adding an adjuvant, (iv) lyophilizing, wherein the vaccine induces protective immunity in swine.

16. The method according to claim 15, wherein the chemical mutagen is MNNG.

17. The method according to claim 15, wherein the cell line comprises CHCC-OU2 deposited as ATCC CRL 12302.

18. A method for propagating a virus that replicates in embryonated eggs, comprising: (a) providing a cell line generated from chicken embryo cells that have been treated with a chemical mutagen to create an immortal cell line said cell line being virus free; (b) infecting said cell line with a virus selected from the group of virus families consisting of Adenoviradae, Birnaviradae, Coronaviradae, Herpesviradae Orthomyxoviradae, Picornaviradae, Poxviradae, Reoviradae, and Polyomaviradae; (c) cultivating the infected cell line to produce an immortal cell line infected with the virus; and (d) removing the virus from the cell line.

19. A method for preparing a vaccine from a virus that replicates in embryonated eggs, comprising: (a) providing a cell line generated from chicken embryo cells that have been treated with a chemical mutagen to create an immortal cell line; (b) infecting said cell line with the virus; (c) cultivating said infected cell line to produce the virus; (d) harvesting the virus from the cultivated cell line; and (e) subjecting the harvested virus to at least one of the following treatments: (i) inactivating the virus, (ii) adding a pharmaceutically acceptable carrier or diluent, (iii) adding an adjuvant, (iv) lyophilizing, wherein the vaccine induces protective immunity in a host animal.

20. A method for preparing a vaccine from a virus that replicates in chicken embryo fibroblasts, comprising: (a) providing a cell line generated from chicken embryo cells that have been treated with a chemical mutagen to create an immortal cell line; (b) infecting said cell line with the virus; (c) cultivating said infected cell line to produce the virus; (d) harvesting the virus from the cultivated cell line; and (e) subjecting the harvested virus to at least one of the following treatments: (i) inactivating the virus, (ii) adding a pharmaceutically acceptable carrier or diluent, (iii) adding an adjuvant, (iv) lyophilizing, wherein the vaccine induces protective immunity in a host animal.

21. A method for propagating a virus that has been modified to replicate in chicken embryo fibroblasts, comprising: (a) providing a cell line generated from chicken embryo cells that have been treated with a chemical mutagen to create an immortal cell line said cell line being virus free; (b) infecting said cell line with the virus; (c) cultivating the infected cell line to produce the virus; and (d) removing the virus from the chicken embryo cell line.

22. A method for preparing a vaccine from a virus that has been modified to replicate in chicken embryo fibroblasts, comprising: (a) providing a cell line generated from chicken embryo cells that have been treated with a chemical mutagen to create an immortal cell line; (b) infecting said cell line with the virus; (c) cultivating said infected cell line to produce the virus; (d) harvesting the virus from the cultivated cell line; and (e) subjecting the harvested virus to at least one of the following treatments: (i) inactivating the virus, (ii) adding a pharmaceutically acceptable carrier or diluent, (iii) adding an adjuvant, (iv) lyophilizing, wherein the vaccine induces protective immunity in a host animal.

23. A method for identifying a virus, comprising: (a) providing a cell line generated from chicken embryo cells that have been treated with a chemical mutagen to create an immortal cell line said cell line being virus free; (b) infecting said cell line with the virus; (c) cultivating the infected cell line to produce the virus; (d) reacting said infected cell line with an antibody specific for the virus; and (e) visualizing infected cells reacted with the antibody.

24. The method according to claim 23, wherein the virus is selected from the group consisting of avian influenza virus, avian reovirus, fowl pox virus, pigeon pox virus, canary pox virus, psittacine herpesvirus, pigeon herpesvirus, falcon herpesvirus, Newcastle disease virus, infectious bursal disease virus, infectious bronchitis virus, avian encephalomyelitis virus, chicken anemia virus, avian adenovirus, swine influenza virus, equine influenza virus, and avian polyomavirus.

25. The method according to claim 23, wherein the chemical mutagen is MNNG.

26. The method according to claim 23 wherein the cell line comprises CHCC-OU2 cells deposited as ATCC CRL 12302.

* * * * *

UNITED STATES PATENT AND TRADEMARK OFFICE

CERTIFICATE OF CORRECTION

PATENT NO. : 5,989,805

DATED : November 23, 1999

INVENTOR(S) : John David Reilly, Daniel C. Taylor, Roger Maes and Paul M. Coussens It is certified that error appears in the above-identified patent and that said Letters Patent is hereby corrected as shown below:

Column 1, line 58, "theses" should be -these-.

Column 2, line 42, "substrate to qualified" should be -substrate to be qualified-.

Column 2, line 49, "loss" should be -lose-.

Column 11, line 22, "mentioned" after "aforementioned" should be deleted.

Column 15, line 40, after "method" and before "present", -of the- should be inserted.

Column 16, line 19, "370oC" should be - 37oC -.

Column 20, line 9, "370oC" should be -37oC -.

Column 24, line 62, "at" after "antiserum" should be deleted.

Column 25, line 52, "at" after "antiserum" should be deleted.

Column 27, line 12, "Avian Polvomavirus" should be -Avian Polyomavirus-.

Column 27, line 18, "CEF cells t" should be -CEF cells it-.

UNITED STATES PATENT AND TRADEMARK OFFICE

CERTIFICATE OF CORRECTION

PATENT NO. : 5,989,805

DATED : November 23, 1999

INVENTOR(S) : John David Reilly, Daniel C. Taylor, Roger Maes and Paul M. Coussens It is certified that error appears in the above-identified patent and that said Letters Patent is hereby corrected as shown below:

Column 27, line 44, "at" after "antiserum" should be deleted.

Signed and Sealed this

First Day of August, 2000

Attest:

Q. TODD DICKINSON

Attesting Officer

*Director of Patents and Trademarks*